US009173656B2

(12) United States Patent
Schurr et al.

(10) Patent No.: US 9,173,656 B2
(45) Date of Patent: Nov. 3, 2015

(54) METHODS AND DEVICES FOR FOLDING AND SECURING TISSUE

(75) Inventors: Marc O. Schurr, Tuebingen (DE); Robert Sakal, Bolton, MA (US); Kurt A. E. Geitz, Sudbury, MA (US); Gerhard Buess, Bebenhausen (DE); Daniel Kalanovic, Munich (DE)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 13/616,212

(22) Filed: Sep. 14, 2012

(65) Prior Publication Data

US 2013/0060264 A1 Mar. 7, 2013

Related U.S. Application Data

(63) Continuation of application No. 09/957,451, filed on Sep. 21, 2001, now abandoned.

(60) Provisional application No. 60/234,360, filed on Sep. 22, 2000.

(51) Int. Cl.
*A61B 17/10* (2006.01)
*A61B 17/08* (2006.01)
(Continued)

(52) U.S. Cl.
CPC ........... *A61B 17/068* (2013.01); *A61B 17/0643* (2013.01); *A61B 17/0644* (2013.01); *A61B 17/00234* (2013.01); *A61B 17/0682* (2013.01);
(Continued)

(58) Field of Classification Search
CPC ............. A61B 17/068; A61B 17/0643; A61B 1/00234; A61B 17/1285; A61B 17/0644; A61B 2017/0647; A61B 2017/0641; A61B 2017/00827; A61B 1/00073; A61B 17/122; A61B 17/0682; A61B 2017/081
USPC .................. 606/139–144, 151, 219–220, 142
See application file for complete search history.

(56) References Cited

U.S. PATENT DOCUMENTS 3,032,039 A 5/1962 Beaty
3,378,010 A 4/1968 Codling et al.
(Continued)

FOREIGN PATENT DOCUMENTS

CA 2 115 131 8/1994
EP 0656191 A2 6/1995
(Continued)

OTHER PUBLICATIONS

J. Barry McKernan et al., "Laparoscopic Antireflux Surgery," The American Surgeon, Jun. 1995, vol. 61, pp. 530-536.

*Primary Examiner* — Jing Ou
(74) *Attorney, Agent, or Firm* — Bookoff McAndrews, PLLC

(57) ABSTRACT

The present invention relates to devices, and methods for using the devices, to create and secure a tissue fold during an endoluminal medical procedure. The devices and methods may be used for folding and securing, for example, a fundus wall onto an esophagus wall or esophageal tissue in the region of the lower esophageal sphincter (LES) to reduce the diameter of the esophagus opening in that region. One aspect of the invention includes forming the tissue fold by closing a grasping arm that is pivotably connected to an overtube that has been positioned at the juncture of the fundus wall and esophagus wall. A further aspect of the invention includes tissue clips configured to be inserted and positioned through an endoluminal device.

18 Claims, 16 Drawing Sheets

(51) Int. Cl.
*A61B 17/068* (2006.01)
*A61B 17/064* (2006.01)
A61B 17/00 (2006.01)
A61B 17/122 (2006.01)
A61B 17/128 (2006.01)

(52) U.S. Cl.
CPC ........... *A61B 17/122* (2013.01); *A61B 17/1285* (2013.01); *A61B 2017/00827* (2013.01); *A61B 2017/0641* (2013.01); *A61B 2017/0647* (2013.01); *A61B 2017/081* (2013.01)

(56) References Cited

U.S. PATENT DOCUMENTS

| | | | |
|---|---|---|---|
| 3,509,882 A | 5/1970 | Blake | |
| 3,604,425 A | 9/1971 | Le Roy | |
| 4,188,953 A | 2/1980 | Klieman et al. | |
| 4,246,903 A | 1/1981 | Larkin | |
| 4,345,600 A | 8/1982 | Rothfuss | |
| 4,346,869 A | 8/1982 | MacNeill | |
| 4,387,489 A | 6/1983 | Dudek | |
| 4,394,864 A | 7/1983 | Sandhaus | |
| 4,402,445 A | 9/1983 | Green | |
| 4,424,810 A | 1/1984 | Jewusiak | |
| 4,449,531 A | 5/1984 | Cerwin et al. | |
| 4,487,205 A | 12/1984 | Di Giovanni et al. | |
| 4,506,669 A | 3/1985 | Blake | |
| 4,512,345 A | 4/1985 | Green | |
| 4,519,392 A | 5/1985 | Lingua | |
| 4,579,118 A | 4/1986 | Failla | |
| 4,635,634 A | 1/1987 | Santos | |
| 4,835,824 A | 6/1989 | Durham et al. | |
| 4,889,119 A | 12/1989 | Jamiolkowski et al. | |
| 4,967,949 A | 11/1990 | Sandhaus | |
| 4,983,176 A | 1/1991 | Cushman et al. | |
| 5,002,562 A | 3/1991 | Oberlander | |
| 5,015,249 A | 5/1991 | Nakao et al. | |
| 5,022,126 A | 6/1991 | Davis | |
| 5,049,153 A | 9/1991 | Nakao et al. | |
| 5,062,846 A | 11/1991 | Oh et al. | |
| 5,100,420 A | 3/1992 | Green et al. | |
| 5,114,065 A | 5/1992 | Storace | |
| 5,171,251 A | 12/1992 | Bregen et al. | |
| 5,171,253 A | 12/1992 | Klieman et al. | |
| 5,201,746 A | 4/1993 | Shichman | |
| 5,207,692 A | 5/1993 | Kraus et al. | |
| 5,236,440 A | 8/1993 | Hlavacek | |
| 5,306,283 A | 4/1994 | Conners | |
| 5,342,394 A * | 8/1994 | Matsuno et al. | 606/213 |
| 5,358,496 A | 10/1994 | Ortiz et al. | |
| 5,395,030 A | 3/1995 | Kuramoto et al. | |
| 5,456,400 A | 10/1995 | Shichman et al. | |
| 5,501,693 A | 3/1996 | Gravener | |
| 5,509,920 A | 4/1996 | Phillips et al. | |
| 5,522,823 A | 6/1996 | Kuntz et al. | |
| 5,540,716 A | 7/1996 | Hlavacek | |
| 5,571,116 A * | 11/1996 | Bolanos et al. | 606/139 |
| 5,620,452 A | 4/1997 | Yoon | |
| 5,626,592 A | 5/1997 | Phillips et al. | |
| 5,649,937 A | 7/1997 | Bito et al. | |
| 5,665,109 A | 9/1997 | Yoon | |
| 5,667,518 A | 9/1997 | Pannell | |
| 5,676,674 A * | 10/1997 | Bolanos et al. | 606/139 |
| 5,676,676 A | 10/1997 | Porter | |
| 5,695,505 A | 12/1997 | Yoon | |
| 5,713,911 A | 2/1998 | Racenet et al. | |
| 5,766,189 A | 6/1998 | Matsuno | |
| 5,833,696 A | 11/1998 | Whitfield et al. | |
| 5,849,019 A | 12/1998 | Yoon | |
| 5,855,565 A | 1/1999 | Bar-Cohen et al. | |
| 5,897,562 A * | 4/1999 | Bolanos et al. | 606/139 |
| 5,916,224 A | 6/1999 | Esplin | |
| 6,051,007 A | 4/2000 | Hogendijk et al. | |
| 6,086,600 A * | 7/2000 | Kortenbach | 606/139 |
| 6,113,609 A * | 9/2000 | Adams | 606/139 |
| 6,126,058 A * | 10/2000 | Adams et al. | 227/180.1 |
| 6,152,935 A * | 11/2000 | Kammerer et al. | 606/144 |
| 6,273,903 B1 | 8/2001 | Wilk | |
| 6,312,437 B1 * | 11/2001 | Kortenbach | 606/139 |
| 6,398,795 B1 * | 6/2002 | McAlister et al. | 606/139 |
| 6,428,548 B1 | 8/2002 | Durgin et al. | |
| 6,517,555 B1 | 2/2003 | Caro | |
| 6,551,328 B2 * | 4/2003 | Kortenbach | 606/139 |
| 6,592,596 B1 * | 7/2003 | Geitz | 606/139 |
| 6,663,640 B2 * | 12/2003 | Kortenbach | 606/142 |
| 6,716,226 B2 | 4/2004 | Sixto, Jr. et al. | |
| 6,923,812 B1 | 8/2005 | Wellisz | |
| 6,986,784 B1 | 1/2006 | Weiser et al. | |
| 2002/0068935 A1 | 6/2002 | Kortenbach et al. | |
| 2002/0068945 A1 | 6/2002 | Sixto, Jr. et al. | |
| 2002/0068946 A1 | 6/2002 | Kortenbach et al. | |
| 2002/0078967 A1 | 6/2002 | Sixto, Jr. et al. | |
| 2002/0082621 A1 * | 6/2002 | Schurr et al. | 606/151 |
| 2002/0138086 A1 | 9/2002 | Sixto, Jr. et al. | |
| 2002/0173786 A1 | 11/2002 | Kortenbach et al. | |
| 2002/0198537 A1 | 12/2002 | Smith et al. | |
| 2002/0198538 A1 | 12/2002 | Kortenbach et al. | |
| 2002/0198539 A1 | 12/2002 | Sixto, Jr. et al. | |
| 2002/0198540 A1 | 12/2002 | Smith et al. | |
| 2002/0198541 A1 | 12/2002 | Smith et al. | |
| 2002/0198549 A1 | 12/2002 | Sixto, Jr. et al. | |
| 2003/0018377 A1 | 1/2003 | Berg et al. | |
| 2003/0036679 A1 | 2/2003 | Kortenbach et al. | |
| 2003/0065340 A1 | 4/2003 | Geitz | |
| 2003/0171760 A1 | 9/2003 | Gambale | |
| 2003/0181929 A1 | 9/2003 | Geitz | |
| 2003/0208209 A1 | 11/2003 | Gambale et al. | |
| 2004/0024386 A1 | 2/2004 | Deem et al. | |

FOREIGN PATENT DOCUMENTS

| | | |
|---|---|---|
| JP | 2007-124166 | 5/2007 |
| WO | WO 99/00059 A1 | 1/1999 |
| WO | WO 00/40159 A1 | 7/2000 |

\* cited by examiner

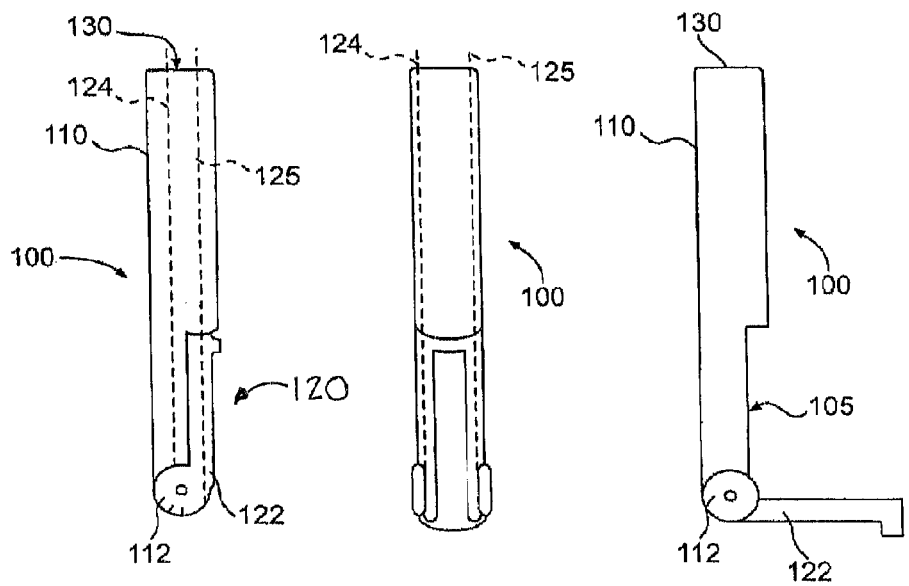
FIG. 2A  FIG. 2B  FIG. 2C
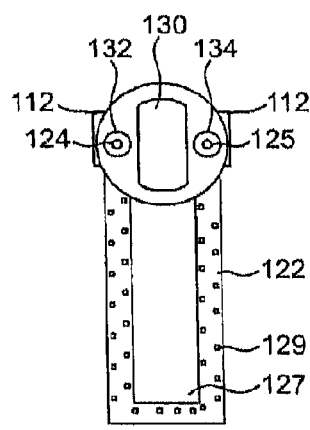
FIG. 2D

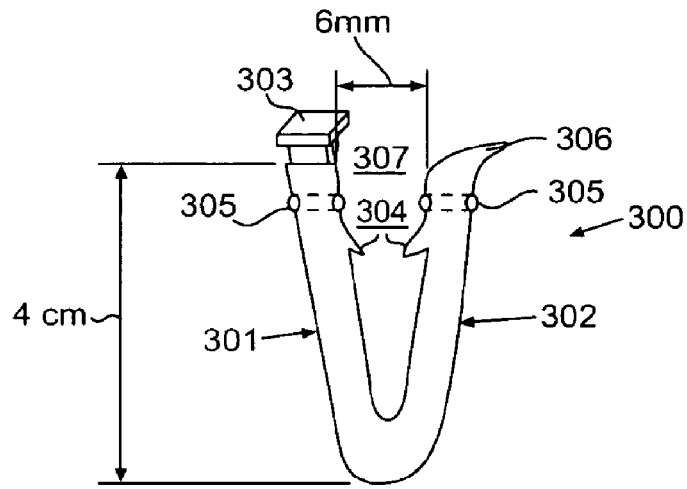
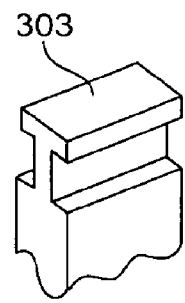
FIG. 6A
FIG. 6B
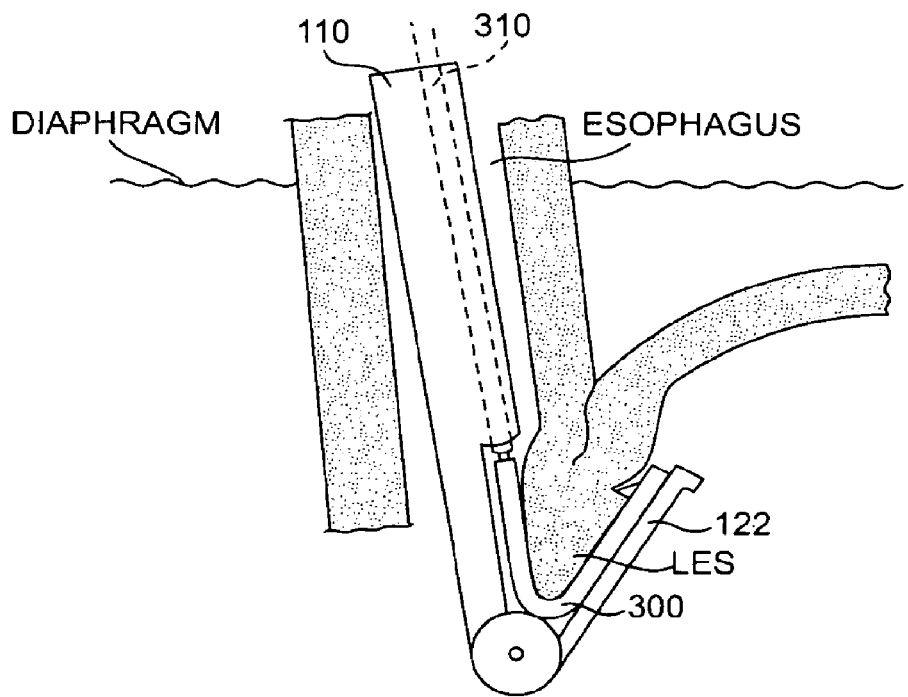
FIG. 7

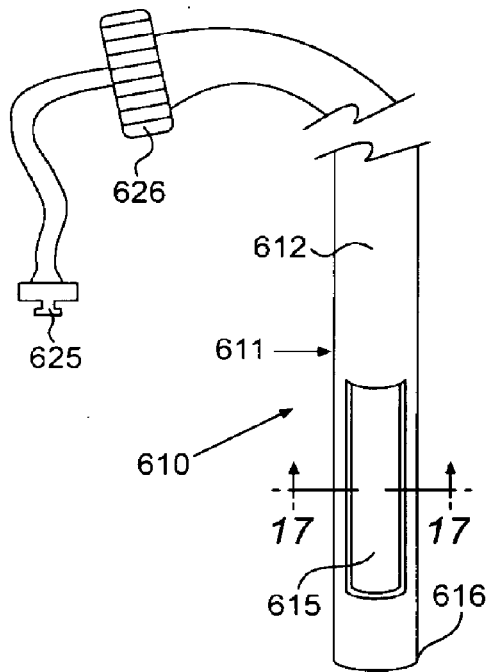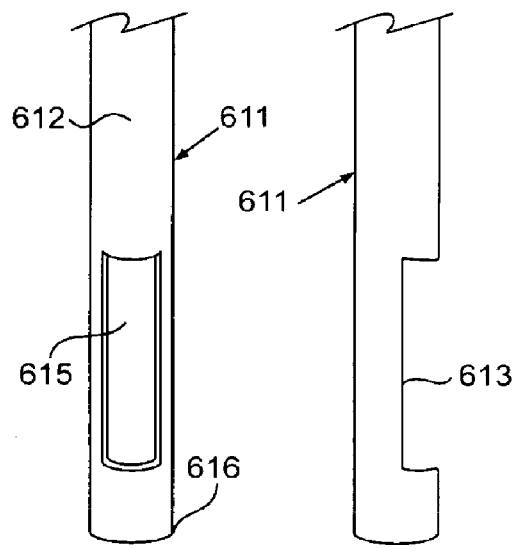
FIG. 15A   FIG. 15B   FIG. 15C
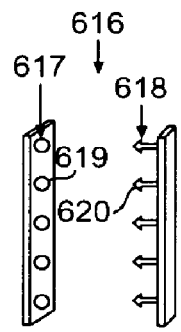
FIG. 16

METHODS AND DEVICES FOR FOLDING AND SECURING TISSUE

CROSS REFERENCE TO RELATED APPLICATIONS

This application is a continuation of U.S. application Ser. No. 09/957,451, filed Sep. 21, 2001, now abandoned which claims the benefit of provisional application No. 60/234,360 filed on Sep. 22, 2000, the contents of all of which are herein incorporated by reference.

FIELD OF THE INVENTION

The present invention pertains to devices, and methods for using the devices, for folding tissue and securing a tissue fold during an endoluminal medical procedure.

BACKGROUND OF THE INVENTION

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1, the LES is a ring of smooth muscle and increased annular thickness existing in approximately the last four centimeters of the esophagus. In its resting state, the LES creates a region of high pressure (approximately 15-30 mm Hg above intragastric pressure) at the opening of the esophagus into the stomach. This pressure essentially closes the esophagus so that contents of the stomach cannot pass back into the esophagus. The LES opens in response to swallowing and peristaltic motion in the esophagus, allowing food to pass into the stomach. After opening, however, a properly functioning LES should return to the resting, or closed state. Transient relaxations of the LES do occur in healthy individuals, typically resulting in occasional bouts of heartburn.

The physical interaction occurring between the gastric fundus and the esophagus also prevents gastroesophageal reflux. The gastric fundus is a lobe of the stomach situated at the top of the stomach proximal to the esophagus. In healthy individuals, the fundus presses against the opening of the esophagus when the stomach is full of food and/or gas. This effectively closes off the esophageal opening to the stomach and helps to prevent acid reflux back into the esophagus.

In individuals with GERD, the LES functions abnormally, either due to an increase in transient LES relaxations, decrease in length of the esophagus, decreased muscle tone of the LES during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not cure the disease completely.

A surgical procedure, known generally as fundoplication, has been developed to prevent acid reflux in patients whose normal LES functioning has been impaired, either as a result of GERD or otherwise. Fundoplication involves bringing the fundus into closer proximity to the esophagus to help close off the esophageal opening into the stomach. In Nissen Fundoplication, a particular type of the fundoplication procedure, the fundus is pulled up and around the esophagus and then sutured to itself and the esophagus such that it completely encircles the esophagus. Traditionally, this procedure has been performed as an open surgery, but has recently enjoyed success as a laparoscopic procedure, as discussed in McKernan, J. B., Champion, J. K., "Laparoscopic antireflex surgery," *American Surgeon*, Vol. 61, pp. 530-536, (1995).

As with any open surgery, complications can occur as a result of infection, blood loss or from the use of anesthesia. Further, the relatively large incisions necessary in the performance of open surgery require extended recovery times for the incision to heal. Though laparoscopic surgical procedures reduce these negative effects by using relatively small devices at a relatively small incision site in the abdominal wall, there still exists an increased risk of infection due to the incision. The location of the incision in the abdominal wall presents a risk of other negative effects, such as sepsis, which can be caused by leakage of septic fluid contained in the stomach.

Other surgical procedures specifically address the LES. These procedures attempt to prevent reflux by thickening the LES region and reducing the diameter of the esophageal opening to the stomach, i.e., tighten the LES region. However, existing procedures are lengthy and difficult to perform.

SUMMARY OF THE INVENTION

The advantages and purpose of the present invention will be set forth in part in the description which follows, and in part will be obvious from the description, or may be learned by practice of the invention. The advantages and purpose of the invention will be realized and attained by means of the elements and combinations particularly pointed out in the appended claims.

The present invention includes devices, and related methods for using the devices, to perform an endoluminal medical procedure. In particular, the inventive devices, and the methods for using the devices, may be employed for the treatment of GERD. The inventive devices and methods allow the procedure to be completed rapidly and repeatedly without compromising safety or increasing invasiveness.

To attain the advantages and in accordance with the purpose of the invention, as embodied and broadly described herein, the invention includes a device for securing a fold of tissue in a medical procedure. The device includes a first arm and a second arm disposed substantially opposite to the first arm and having an end connected to an end of the first arm. Thus connected, the arms define an opening to receive the fold of tissue. The arms are configured to secure to a tissue fold with the arms remaining exterior to an outer surface of the tissue fold.

According to another aspect of the present invention, a method for securing a tissue fold during an endoluminal medical procedure includes inserting an endoluminal device proximal to the tissue to be folded, folding tissue together to create a tissue fold, and inserting a tissue clip through the endoluminal device. The tissue clip is then positioned such that the fold is placed in an opening defined by the clip, and engaged with the tissue fold.

Yet another aspect of the present invention is a working end of an endoluminal device for use in an endoluminal medical procedure. The working end includes a plurality of interconnected members having an expandable working surface area configured to engage with a portion of the body to perform the medical procedure.

According to another aspect of the present invention, there exists a device for creating a tissue fold in an endoluminal medical procedure. The device includes a tube defining a channel extending in a longitudinal direction from a proximal end to a distal end of the tube. An expandable arm is pivotably disposed on the distal end of the tube. The arm is configured to pivot between a position substantially along the longitudinal direction and a position angled to the longitudinal direction. The arm is expandable from a retracted configuration to an expanded configuration.

According to a further aspect of the present invention, a method for creating a tissue fold during an endoluminal procedure includes providing a tube and an expandable arm pivotably connected to a distal end of the tube, the tube and the arm are configured to be inserted into the body to perform a medical procedure. The method further includes inserting the tube in the body while the expandable arm is positioned along the tube and retracted. After insertion, the arm is pivoted away from the tube and expanded. The arm is then positioned under the tissue to be folded, and pivoted toward the tube to fold the tissue.

Another aspect according to an embodiment of the present invention includes a device for securing a tissue fold. The device includes a mounting member having a peripheral surface. The mounting member includes a plurality of first engagement portions disposed about the peripheral surface. The device further includes a plurality of tissue securing members configured to engage the mounting member at the first engagement portions.

Another aspect according to an embodiment of the present invention includes a method for securing a tissue fold. The method includes providing a mounting member having a peripheral surface with a plurality of first engagement portions disposed about the peripheral surface. A plurality of tissue securing members are also provided and are adapted to engage the mounting member at the first engagement portions. The method further includes installing the mounting member and tissue securing members endoluminally and proximal to the tissue fold. The tissue securing members are then positioned on exterior surfaces of the tissue fold and engaged with the first engagement portions to secure the tissue securing members in place with respect to the tissue fold and the mounting member.

Another aspect according to an embodiment of the present invention includes a device for securing a fold of tissue. The device includes a tube defining a lumen therein and an opening proximate a distal end of the tube. The tube is configured to draw suction through the lumen and accommodate tissue to be secured into the opening. A holding member is disposed in the lumen and is configured to hold a tissue clip that secures the tissue. A member is disposed in the lumen and configured to actuate relative to the tube between an open position and a closed position to open and close the tube opening. The tissue clip is installed by the relative actuation.

Yet another aspect of the invention includes a method for securing a tissue. The method includes providing a tube defining a lumen therein and an opening proximate a distal end of the tube. The method further includes positioning the opening proximal to tissue to be secured together and drawing tissue through the opening by application of suction through the lumen. After the tissue is drawn the opening, a member disposed within the lumen is actuated to install a tissue clip to secure the tissue together.

According to still yet another aspect of the present invention a device for securing tissue in a medical procedure includes a cannula having a proximal end, a distal end, and a longitudinal window located adjacent the distal end, a suction device for creating a vacuum through the cannula and to the window, the suction urging tissue into the window, and a grasping element located in the cannula and movable between a non-grasping position where the element is outside a boundary of the window to a grasping position where the grasping element is within the boundary of the window.

Yet another aspect of the present invention includes a method for treating gastro-esophageal reflux disease including the steps of introducing a cannula into the stomach cavity, inserting a suction-grasper device into a lumen of the cannula and securing tissue in the suction-grasper device, urging the secured tissue toward a distal end of the cannula, releasing the secured tissue so that it can be grasped between the cannula and a grasping element located at the distal end of the cannula, and fixedly attaching the grasped tissue to a tissue wall of the patient.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the preferred embodiments of the invention and, together with the description, serve to explain the principles of the invention. In the drawings.

FIGS. 2A-2C are a respective side view of an A-frame grasper-overtube with the grasping arm in a closed position and a front view and a side view of the A-frame grasper-overtube with the grasping arm in an open position;

FIG. 2D is a top view of an A-fram grasper-overtube with the grasping arm in an open position;

FIG. 6A is a planar view of a tissue clip according to an embodiment of the present invention;

FIG. 6B is an enlarged view of the gripping tab of the tissue clip of FIG. 6A;

FIG. 7 is a cross-sectional view of a portion of the esophagus and stomach with a side view of an A-frame grasper-overtube actuated to fold the fundus wall onto the esophagus wall and a side view of a tissue clip according to an embodiment of the present invention inserted through the grasper-overtube to secure to the tissue fold created in the fundoplication procedure;

FIGS. 15A-15C are perspective open front, closed front, and open side views of a suction stapler according to an embodiment of the present invention;

FIG. 16 is an embodiment of respective male and female parts of a tissue clip to be used with a suction stapler according to an embodiment of the present invention;

DESCRIPTION OF THE PREFERRED EMBODIMENTS

Figure 1:
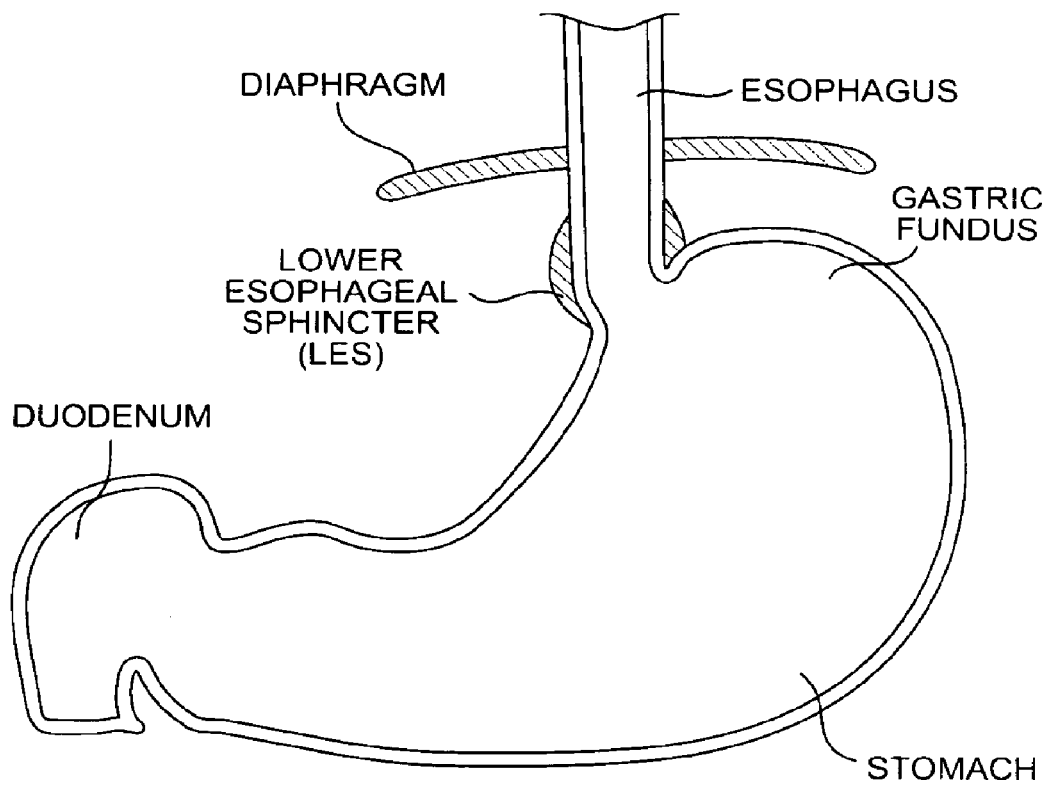
FIG. 1 is a cross-sectional view of the gastrointestinal tract from a mid-point of the esophagus to a point near the beginning of the duodenum.

A newly developed form of fundoplication, referred to as Endoscopic Fundoplication, is an endoluminal procedure in which the fundus wall is folded back onto the esophagus wall. The tissue fold formed between the esophagus and the fundus then is secured. Endoscopic Fundoplication is intended to be performed as an endoluminal procedure in which insertion of required medical instruments occurs through the esophagus. Such a procedure has the benefits of being less invasive, quicker, and less expensive as compared to previous techniques.

A device currently employed in Endoscopic Fundoplication is shown in FIGS. 2A-2C. This device, referred to as an A-frame grasper-overtube 100, includes an overtube 110 with a cable-actuated grasper 120 at a distal end of the device. Cable-actuated grasper 120 includes a grasping arm 122 attached to the distal end of overtube 110 by a pivot 112. Overtube 110 includes a lumen 130, preferably having a diameter capable of accommodating a 6 mm-diameter articulating endoscope, as well as other endoluminal devices. Overtube 110 is preferably made of metal reinforced plastic and is flexible. At its distal end, near grasper 120, overtube 110 includes a large opening 105 disposed in a sidewall of overtube 110. Opening 105 accommodates grasping arm 122 such that, in an insertion position of the A-frame grasper-overtube 100, grasping arm 122 essentially closes opening 105 and lies substantially flush with the rest of the overtube sidewall that defines opening 105. Grasping arm 122 also includes an elongated slot or opening 127 extending substantially longitudinally in the center of the arm and a plurality of protrusions 129 for assisting in grasping the tissue.

The insertion or closed position is shown best in FIG. 2a. Grasping arm 122 of A-Frame grasper-overtube 100 may be actuated or opened by pulling a first cable 124 attached at the proximal end of grasping arm 122 at or adjacent pivot 112 and running up through a lumen 132 in overtube 110 to a proximal end of the device. The pulling motion of first cable 124 causes grasping arm 122 to rotate about pivot 112 to thereby form an increasing angle between grasping arm 122 and overtube 110. FIG. 2C shows grasping arm 122 in an actuated or open position and forming approximately a 90 degree angle with overtube 110. A second cable 125 may also be attached at the proximal end of grasping arm 122 and running up through a lumen 134 in overtube 110 to a proximal end of the device. Second cable 125 is actuatable to rotate grasping arm 122 from an open position to a closed position. Pulling of second cable 125 causes grasping arm 122 to rotate about pivot 112 in a direction opposite that caused by pulling on first cable 124, and thus reducing the angle formed between grasping arm 122 and overtube 110 toward the completely retracted position shown in FIG. 2a. First and second cables 124, 125 may run through a combined or separate channels 132, 134 formed in overtube 110 and extending from a proximal end to a distal end of the device. Alternatively, one cable may extend from a proximal end of overtube 110, connect to grasping arm 122, loop around pivot 112, and extend back to the proximal end of overtube 110. In this arrangement, the cable would have two proximal ends and pulling one end of the proximal ends of the cable would cause retraction of the grasping arm 122, and pulling the other proximal end of the cable would cause opening of the grasping arm 122.

Distal end of overtube 110 may include a clear section formed opposite opening 105. Clear section would allow for visual confirmation of the location of tissue intended to be folded by A-frame grasper-overtube 100. Such visual confirmation could be achieved by way of, for example, an endoscope. Alternatively, the whole overtube 110 may be fabricated of a clear material.

Using the grasper-overtube shown in FIGS. 2A-2C, Endoscopic Fundoplication is performed in the following manner. In the insertion position shown in FIG. 2A, grasper-overtube 100 is inserted into the stomach through the esophagus. Insertion of grasper-overtube 100 continues until the distal end of the grasper-overtube 100 reaches a point within the stomach below the fundus. Grasper-overtube 100 preferably is inserted with the sidewall containing opening 105 facing toward the fundus. However, it is contemplated that after insertion, grasper-overtube 100 can be rotated about its longitudinal axis to the desired position. An endoscope may be extended through lumen 130 in overtube 110 to provide vision within the stomach after insertion of grasper-overtube 100. Preferably, a 6 mm-diameter articulating endoscope is used, however the size and type of endoscope can be selected depending on the particularities associated with the procedure being performed.

Figure 3:
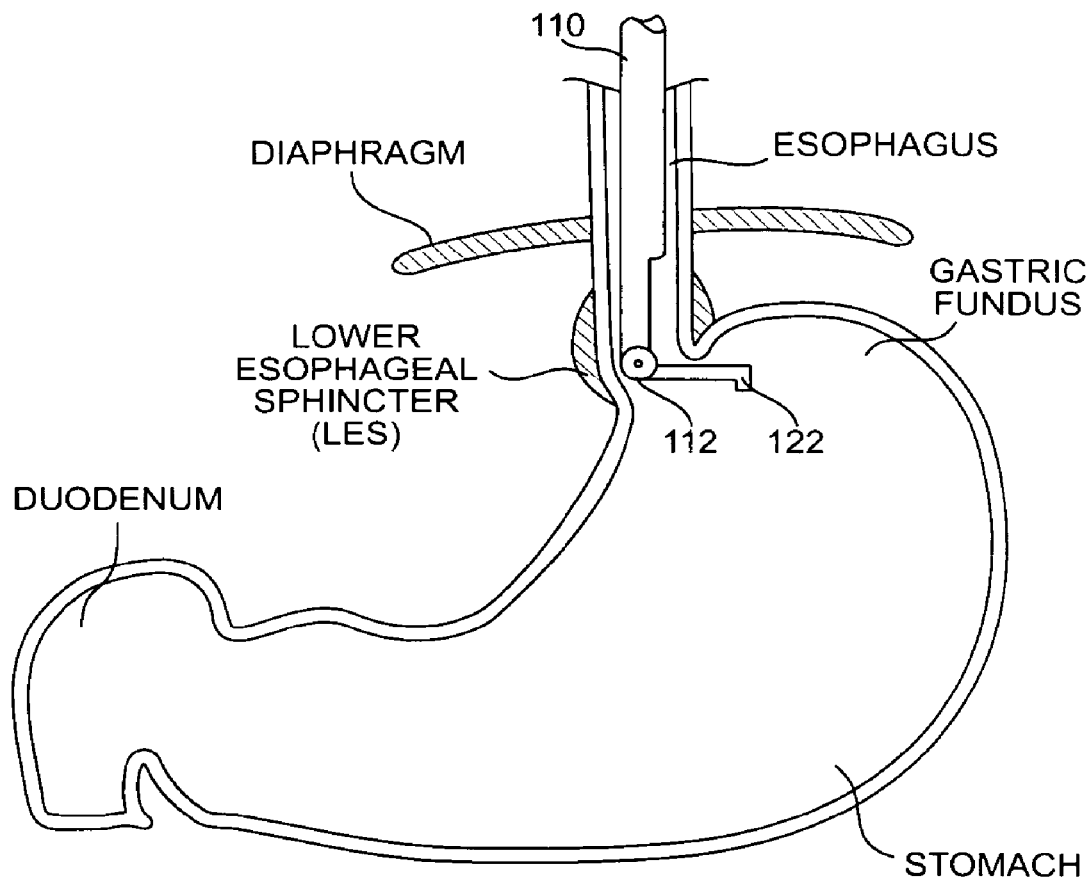
FIG. 3 is a cross-sectional view of a portion of the esophagus and stomach with the A-frame grasper-overtube inserted to perform a fundoplication procedure.
Figure 4:
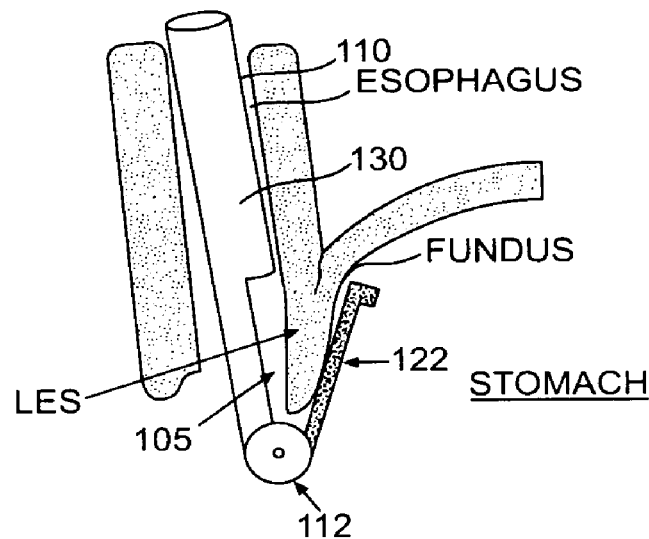
FIG. 4 is a cross-sectional view of a portion of the esophagus and stomach with a side view of an A-frame grasper-overtube actuated to fold the fundus wall onto the esophagus wall during a fundoplication procedure.

After inserting and positioning overtube 110 to the desired location below the fundus, grasping arm 122 is actuated and pivots downward to its open position approximately perpendicular to overtube 110, as shown in FIG. 3. Grasper-overtube 100 is then lifted upward toward the opening of the esophagus in the stomach. Next, cable 124 is actuated to return grasping arm 122 to its closed position. The arcing motion of grasping arm 122 as it engages the wall of the fundus, causes the fundus to fold against the side of the esophagus near its opening into the stomach, as illustrated in FIG. 4. After the fundus wall has been folded back onto the esophagus wall, it is secured into place and grasper-overtube 100 is removed.

After the fold has been created, securing the fundus can be accomplished using a variety of fastening mechanisms such as, for example, sutures, clips, staples, or other suitable like mechanisms. It is desirable that the fastening mechanisms selected can be installed relatively quickly in a relatively non-invasive manner, and can create a substantially uniform fold of tissue once installed.

As with most endoluminal procedures, Endoscopic Fundoplication is preferably completed as rapidly as possible without compromising the safety or non-invasiveness of the procedure. To maintain the procedure as relatively non-invasive, any device used in the procedure should be small, yet preferably have a working size adaptable to the particular circumstances that may be present during any individual procedure, such as, the particular size and anatomy of a patient. An additional goal of Endoscopic Fundoplication involves the ability to implement the procedure repeatedly.

Various aspects of this invention pertain generally to devices to be used in conjunction, for example, with an A-frame grasper-overtube to perform a Endoscopic Fundoplication procedure. The inventive devices include improvements to the A-frame grasper-overtube so that Endoscopic Fundoplication can be performed repeatedly and more quickly, without degrading the safety or non-invasiveness of the procedure. Moreover, the inventive devices to be disclosed can be inserted into endoluminal devices having limited lumen diameters and can be used in patients of varying sizes and anatomies.

To accomplish these objectives, the present invention includes a tissue clip device and an expandable grasping arm. Preferably, both of the inventive devices are capable of being used with the A-frame grasper-overtube described in connection with FIGS. 2-4, though use of the devices other than with the grasper-overtube are within the scope of this invention. Additionally, the present invention includes respective methods for using the tissue clip and the expandable grasping arm.

Figure 5:
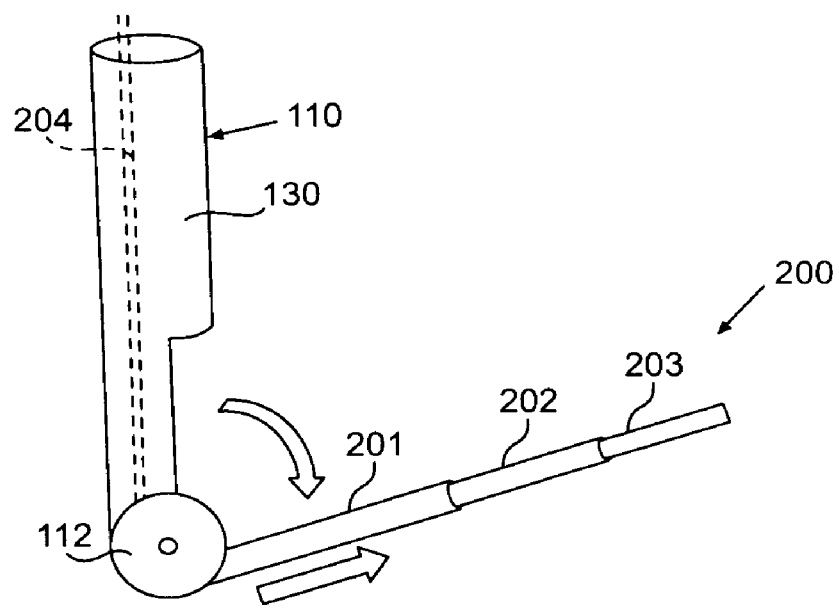
FIG. 5 is a side view of an expandable grasping arm according to an embodiment of the present invention, with the arm disposed on the distal end of an A-frame grasper-overtube.

An embodiment of an expandable grasping arm according to the present invention is shown in FIG. 5. Expandable grasping arm 200 is shown in conjunction with A-frame grasper-overtube 100. However, the expandable grasping arm can be used with other devices as well. The various structural features of A-frame grasper-overtube 100 of FIG. 5, with the exception of grasping arm 200 and the structure required to operate the arm to be described, are the same as those disclosed in the description of overtube 100 of FIG. 2, and have the same reference numerals to indicate identical parts.

In the preferred embodiment shown, expandable grasping arm 200 includes hollow tubes 201-203, shown in FIG. 5. Tubes 201-203 engage each other in a telescoping relationship to extend and retract grasping arm 200. A lumen (not shown) formed by tubes 201-203 receives a hydraulic fluid supplied by a syringe into a proximal end of overtube 110. The fluid can be supplied by a syringe or other suitable supplying device into a tube 204 extending through a lumen formed in overtube 110 that opens into the lumen within tubes 201-203 of grasping arm 200. The increased pressure in the tubes that results from the feeding of the hydraulic fluid into the lumen of tubes 201-203 causes the tubes to slide outward to extend the grasping arm 200. In a fully-expanded configuration, tubes 201-203 essentially are disposed in an end-to-end relationship. By removing the fluid pressure in tubes 201-204, grasping arm 200 can be retracted. In a fully-retracted configuration, tubes 201-203 are disposed in a substantially concentric relationship.

Although three tubes are shown in the embodiment of the expandable grasping arm 200 shown in FIG. 5, it is considered within the scope of the invention to provide more or less than three tubes. Selection of the number of tubes depends on various parameters of the procedure to be performed, such as, for example, the length of the fold and the size of the lumen diameter of the grasper-overtube. However, the overall length of the grasping arm should not exceed that which is required to maintain the mechanical advantage of the device when creating the fold of tissue.

The scope of the present invention includes a grasping arm that includes other expandable structures. For example, rather than providing a telescoping arrangement of tubes, a telescoping ladder configuration may be provided. Such an embodiment would operate similar to the embodiment of FIG. 5, however, instead of hydraulic actuation, each arm segment could be coupled to an actuating wire or wires to extend or retract the grasping arm.

The use of shape memory materials, inflatable members, and folding members, as opposed to the hydraulic telescoping members, in making the expandable grasping arm also is contemplated by the present invention.

The following describes the use of the inventive expandable grasping arm to create a tissue fold. As discussed with reference to FIG. 3, the A-frame grasper-overtube is inserted into the body to a point below the fundus. Expandable grasping arm 200 is actuated in a manner similar to the grasping arm 122. That is, a cable is actuated, causing pivot 112 to rotate expandable grasping arm 200 in a downward direction until it is substantially perpendicular with overtube 110. During this actuation step, tubes 201-203 are in their fully-retracted configuration. After pivotable actuation of expandable grasping arm 200, grasping arm 200 is extended by feeding a hydraulic fluid through the channel in the overtube and the lumen formed by tubes 201-203. Expandable grasping arm 200 can be extended to a length suitable for the patient's anatomy and for the desired depth of folded tissue. Upon extending grasping arm 200 to the proper length, the cable is actuated again to rotate grasping arm 200 in an upward motion to create and hold the fold formed by the fundus and esophagus walls in place. Once the fold of tissue has been held in place with the use of the expandable grasper, clips, staples, sutures, or other securing mechanisms may be used to secure the fundus to the esophagus to complete the fundoplication procedure. Tissue clips 300 disclosed below can be used to secure the fundus to the esophagus in a Endoscopic Fundoplication procedure. After the fold is secured, expandable grasping arm 200 can be rotated downward to release the fold of tissue and arm 200 can be retracted lengthwise by reversing the feed of hydraulic fluid out of tubes 201-203 and overtube 110.

It will be apparent to those skilled in the art from consideration of the specification and practice of the invention disclosed herein that various modifications and variations can be made in the expandable grasping arm of the present invention. For example, the overall length of the grasper arm may vary according to the configuration of the endoluminal device with which it is employed.

An embodiment of a tissue clip 300 according to the present invention is shown in FIG. 6A. Tissue clip 300 is configured to secure the fundus wall to the outer wall of the esophagus proximal to the opening of the esophagus into the stomach. Thus, tissue clip 300 may be used to complete a fundoplication procedure, and specifically a Endoscopic Fundoplication procedure. Tissue clip 300 essentially includes two arms, 301 and 302, connected to each other so as to have a substantially U-shaped configuration. Arms 301 and 302 preferably connect to one another such that when disposed to secure the tissue fold in the fundoplication procedure, each arm 301 and 302 will frictionally engage with a surface of the fold. This frictional engagement preferably establishes a compressive force on the folded tissue to hold the tissue together.

Tissue clip 300, as shown in FIG. 6A, includes a gripping tab 303 for grasping during installation of tissue clip 300. Gripping tab 303 allows tissue clip 300 to be held by a deployment device 310 (FIG. 7) having a distal end configured to mate with gripping tab 303. When tissue clip 300 is positioned on the fold of the tissue appropriately, deployment device 310 will release gripping tab 303. Tissue clip 300 further includes reverse-angle stabilizing barbs 304 disposed on opposing inner surfaces of the clip. Barbs 304 help to prevent the clip from moving relative to the tissue fold and assist in holding tissue clip 300 in place should the frictional engagement between the clip and the fold be overcome. Fixation holes 305 also may be disposed on each arm 301 and 302 of tissue clip 300 so that, if necessary, clip 300 may be anchored to the tissue. Anchors may be provided in the form of pins, bolts, sutures, staples, biodegradable rods or other suitable anchoring devices. As shown, two barbs 304 are disposed on tissue clip 300, with one barb on each inner surface of arms 301 and 302. The barbs 304 are positioned directly opposite to one another. However, it is contemplated that more than one barb can be disposed on each inner surface of clip 300 and can be positioned such that they are spaced vertically from one another. One having ordinary skill in the art would recognize that the exact number and placement of the barbs can vary according to factors such as, for example, the thickness of the tissue to be secured, the exact placement of the tissue clip, the clip material, the number of total clips desired to secure the tissue, and other similar factors.

In the embodiment of tissue clip 300 shown in FIG. 6A, arm 301 extends in a substantially vertical direction when the clip is grabbed by gripping tab 303. Arm 302 connects to arm 301 at a slight angle such that the opening formed between arms 301 and 302 is slightly tapered, with the widest portion of the taper occurring at the proximal ends of the arms. One of arms 301 or 302 also may have a slight crook 306 at its proximal end for the purpose of providing a surface to push against to bring the arms closer together during insertion. The crook 306 also may be used to permit smooth, easy insertion of tissue fold into clip 300 by sliding the fold along the inner surface of crook 306. Preferably, crook 306 is disposed on the arm that does not include gripping tab 303.

Tissue clip 300 can be made of any suitable material that is biocompatible, such as titanium, polyethylene, teflon or ABS. Preferred materials include bioabsorbable materials, such as, polylactic acid or polyglycolic acid. When a bioabsorbable material is used to make tissue clip 300, it is contemplated that eventually the tissue on the walls of the esophagus and the fundus will adhere together such that external securing means, such as the clip, are unnecessary. Thus, the bioabsorbable material should be selected such that disintegration of the clip occurs after the tissue of the fold has had an opportunity to fully adhere. A material to be selected for clip 300 may be one that results in some frictional engagement between the esophogeal and fundus tissue and the surface of clip 300. For example, the surface of clip 300 can be textured for the purpose of enhancing the frictional engagement.

In general, tissue clip 300 has dimensions that allow it to be used with endoluminal devices and for the purposes of securing the fold created during a fundoplication procedure. One form of tissue clip 300 has dimensions that enable it to be inserted and installed using an A-frame grasper-overtube 100. Thus, tissue clip 300 preferably has a length of approximately 4 centimeters, as measured from the apex of the U to the ends of arms 301 and 302. An opening 307 at the mouth of clip 300 preferably is approximately 6 millimeters measured between the inner surfaces of arms 301 and 302. Dimensioned in this way, tissue clip 300 will fit within lumen 130 of the A-frame grasper-overtube described in connection with FIGS. 2-4. However, such dimensions are meant to be exemplary only and the particular dimensions may vary according to the design of the particular A-frame grasper-overtube used to perform the procedure or to whether the clip is used in conjunction with other delivery devices. The method of using tissue clip 300 to perform Endoscopic Fundoplication will now be described, with reference to FIG. 8. First, A-frame grasper-overtube 100 is implemented according to the steps described in connection with FIGS. 2-4 such that grasping arm 122 has been actuated to complete the folding of the fundus wall onto the esophagus wall. Then, tissue clip 300 is inserted through lumen 130. Any standard gripper may be used to grasp tissue clip 300 by gripping tab 303 to insert the tissue clip through lumen 130 of grasper-overtube 100. Tissue clip 300 is lowered through opening 105 to a position below the fold of the tissue, which continues to be held in place via grasping arm 122. The dimensions of tissue clip 300 allow arms 301 and 302 to be placed on opposite sides of the fold of tissue such that arm 301 rests within opening 105 and arm 302 rests within the opening of grasping arm 122, as shown most clearly in FIG. 7 where tissue clip 300 has been engaged with the tissue fold created by grasper-overtube 100. Once positioned such that the apex of the tissue fold enters opening 307 of tissue clip 300, the clip, by way of the gripper, is pulled upward in a firm motion to seat the fold of tissue fully into the clip. Barbs 304 will engage outer surfaces of the tissue fold to inhibit movement of tissue clip 300 is relative to the tissue fold. If necessary, tissue clip 300 can be anchored to the tissue using an anchoring member through fixation hole 305.

Figure 8:
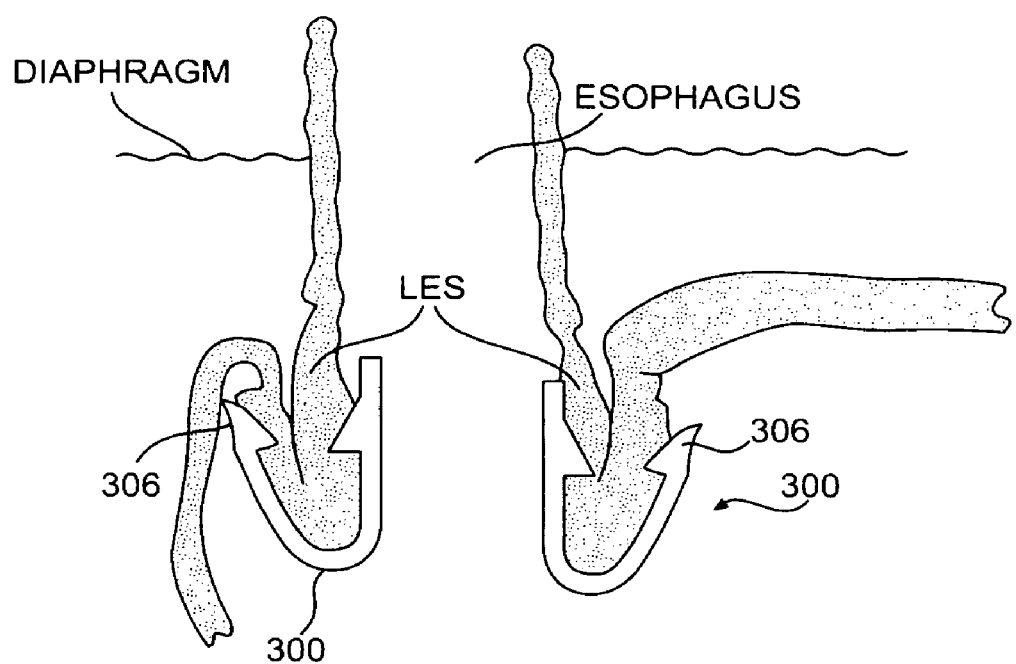
FIG. 8 is a cross-sectional view of a portion of the esophagus and stomach with two tissue clips shown securing the fundus to the esophagus according to an embodiment of the present invention.

After tissue clip 300 is secured in place to hold the fold of tissue, cable 124 can be actuated to cause grasper arm 111 to assume an open position to release the fold of tissue. A-frame grasper-overtube 100 then can be removed from the area of the fold. If more than one tissue clip is needed to complete the fundoplication procedure, A-frame grasper-overtube 100 can be rotated to a new position and the process described above for folding and securing tissue can be repeated. Tissue clips may be installed around the entire circumference of the esophageal opening to hold the folded fundus into place. Thus, using the tissue clip of the present invention, a fundoplication procedure such as Endoscopic Fundoplication can be completed relatively quickly and non-invasively. The securing of the fundus wall to the esophagus wall can be completed entirely through the use of a single endoluminal device, requiring only a single point of insertion on the body. Additionally, the U-shaped configuration of tissue clip 300 results in a more uniform geometry associated with the fold because the clips essentially provide a consistent template for the depth of tissue that will be secured. FIG. 8 shows an example of a completed Endoscopic Fundoplication procedure with two tissue clips 300 used to secure the fundus to the esophagus.

As a final step in the method of using tissue clip 300, a sclerosing agent may be injected into the folds to promote the natural adhesion of the fundus to the esophagus. If tissue clips 300 are made from a bioabsorbable material, they will eventually disintegrate. Preferably, the bioabsorbable material chosen for tissue clip 300 disintegrates over a time period longer than is required for natural adhesion to occur.

It will be apparent to those skilled in the art from consideration of the specification and practice of the invention disclosed herein that various modifications and variations can be made in the tissue clip of the present invention. For example, the tissue clip may be provided in different sizes, for example, small, medium, and large, for use with children, average-sized, and larger patients, respectively.

Furthermore, the particular use of both the tissue clip and the grasper arm in conjunction with the A-frame grasper-overtube device and Endoscopic Fundoplication procedure are illustrative only. It is considered to be within the scope of this invention to use these devices with other endoluminal procedures, as well as for purposes outside of the medical industry that may require insertion and installation of fasteners or material grabbing devices through small spaces.

Figure 9:
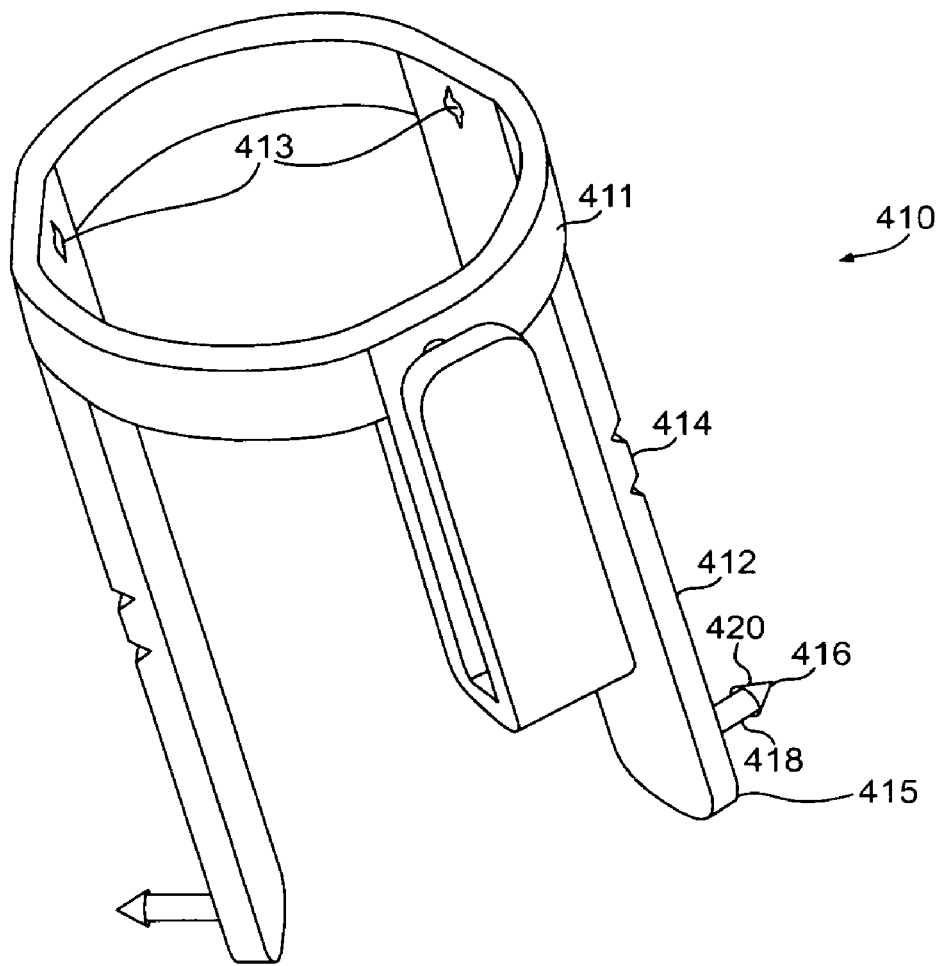
FIG. 9 is a planar view of a mounting device according to an embodiment of the present invention, with one of the legs of the device engaged with an aperture of the ring.
Figure 10:
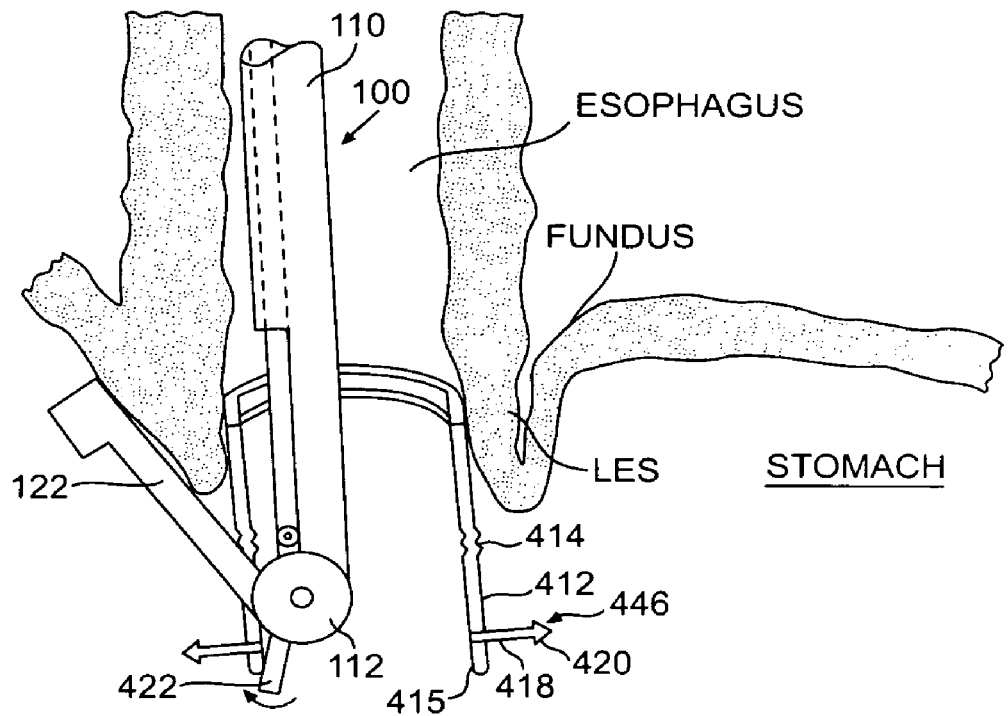
FIG. 10 is cross-sectional view of a portion of the esophagus leading into the stomach with the mounting device of FIG. 9 shown in place with respect to a tissue fold created between the fundus wall and the esophagus wall prior to folding the legs of the mounting device and engaging the legs with the apertures.
Figure 11:
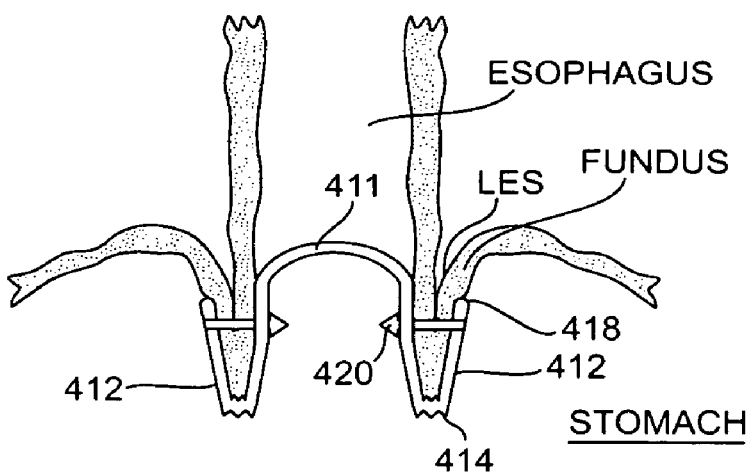
FIG. 11 is a vertical cross-sectional view of a mounting device of FIG. 9 installed to secure a tissue fold formed by the fundus wall and esophagus wall.

An embodiment of a mounting device 410 according to the present invention is shown in FIGS. 9-11. The mounting device includes a ring 411 preferably having an outer peripheral surface forming a substantially circular shape as shown. Ring 411 is configured to be inserted into the esophagus during an endoluminal procedure. To facilitate insertion through a narrow passage associated with an endoluminal device or through the esophagus itself, ring 411 preferably is made of a flexible or elastic material, such as silicone and polyurethane. Furthermore, the dimensions of ring 411 allow the ring to be inserted through a narrow passage and placed within a base portion of the esophagus near its opening into the stomach. For example, ring 411 may have a diameter of approximately 18 mm. In particular, the outer peripheral surface of ring 411 preferably establishes a frictional fit with the inside of the esophagus without impeding the esophageal passageway. Alternatively, ring 411 may be affixed to the inside of the esophagus through sutures or other suitable fixation means. Ring 411 should be positioned within the esophagus such that the longitudinal axis of the ring and the esophagus are substantially colinear. Using an elastic or flexible material for ring 411 also allows the esophagus to close to prevent reflux.

Ring 411 further includes at least one engagement portion disposed on the peripheral surface of the ring. In the embodiment shown in FIG. 9, an aperture 413 extends through the peripheral surface of the ring in a direction perpendicular to the ring's longitudinal axis. Further shown in FIG. 9, ring 411 preferably defines three apertures 413 evenly spaced around the circumference of the ring. At locations around ring 411 corresponding to apertures 413, legs 412 depend from ring 411. Legs 412 extend in a direction essentially parallel to the longitudinal axis of ring 411. Legs 412 can depend either from a bottom of ring 411, as shown, for example, in FIG. 9 or from a peripheral surface of the ring. Each leg 412 includes a grooved region 414 located approximately midway along its length. Grooved region 414 forms a hinge to allow legs 412 to fold easily around a tissue fold. At a free end 415, each leg 412 includes an engagement member 416 configured to engage aperture 413. Engagement member 416 protrudes from leg 412 in a direction perpendicular to the leg and away from the longitudinal axis of ring 411. Although there are three apertures and corresponding legs shown in FIG. 9, any number of apertures and corresponding legs can be provided depending on the desired fold configuration, the thickness of the fold, and other similar factors.

Engagement member 416 and aperture 413 are configured such that, prior to their engagement, engagement member 416 is capable of insertion through aperture 413. After engagement member 416 has been inserted into aperture 413, however, engagement member 416 is restricted from passing back through aperture 413 in a direction opposite to that of initial insertion. Thus, according to one embodiment of the invention, engagement member 416 includes a shaft portion 418 and a tapered head 420, with the widest portion of tapered head 420 adjacent shaft 418. At its free end, tapered head 420 is configured to pierce the tissue fold to be secured. Shaft 418 has a length long enough to extend through a tissue fold. During insertion, the free end of head 420 will pass through aperture 413 first. Once the widest portion of head 420 has passed through aperture 413, attempting to pass engagement member 416 back through aperture 413 in a direction opposite to insertion will cause the widest portion of head 420 to abut the inner surface of ring 411. This restricts engagement member 416 from disengaging aperture 413. Aperture 413 preferably has the shape of a slotted hole or an X, or other similar suitable configuration that allows passage of head 420 during insertion but restricts passage after insertion.

Figure 9A:
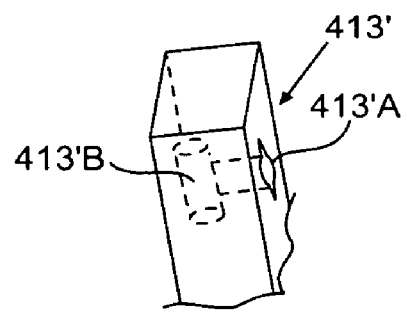
FIG. 9A is a perspective view of an engagement recess that can be used instead of an aperture to engage the legs and the ring of the mounting device.

As shown in FIG. 9A, apertures 413, which extend entirely through ring 411, can be replaced with engagement recesses 413'. Each engagement recess 413' extends only partially through ring 411 and includes a widened opening 413'B within the depth of ring 411. In this manner, tapered head 420 of engagement member 416 would be inserted through recess opening 413'A in the direction toward the widened opening 413'B, but would be prohibited from passing back through in an opposite direction. That is, the wide portion of the head 420 would abut against the interior surface between widened opening 413'B and recess opening 413'A.

Furthermore, apertures 413 or recesses 413' could be disposed on the tissue securing members, and engagement members 416 disposed on the ring. In this case, preferably ring 411 will include a housing recess, or other protection mechanism, to protect the esophagus from being damaged by the sharp portion of head 420 as ring 411 is inserted. In such an embodiment, an actuator could place the engagement members into positions perpendicular to the ring peripheral surface when the tissue is ready for securing.

In the embodiment shown in FIGS. 9-11, ring 411 and legs 412 form an integral device. The entire device can be formed as either a single-molded piece or legs 412 can be fixedly attached to ring 411 using an adhesive or other suitable fastening means apparent to one having ordinary skill in the art.

Ring 411 and legs 412 can be made of any suitable material that is biocompatible, and at least for an initial time period resistant to degradation from acids and other substances passing through the esophagus. Preferably, a bioabsorbable material is used so that the device will disintegrate after a certain time period sufficient for the natural adhesion of the tissue of the tissue fold to occur. Ring 411 may be made of a different material than legs 412, for example, ring 411 may be formed of a flexible material such as silicone or polyurethane, while legs 412 may be formed of bioabsorbable material such as polyactic acid or polyglycolic acid. In this way, ring 411 can have sufficient flexibility to allow the esophagus to close, while legs 412 have sufficient rigidity to secure the tissue fold. Further, ring 411 can be dimensioned to pass through the digestive tract so as not to cause complications if ring 411 were to be separated from legs 412.

Installation of mounting device 410 during an endoluminal procedure, such as, for example Endoscopic Fundoplication, will now be described. With legs 412 in their extended position, mounting device 410 is inserted through the esophagus. An endoluminal device, such as, for example, a flexible tube carrying ring 411 on its exterior, can be used to insert mounting device 10 into the esophagus. During insertion, it is important that heads 420 of engagement members 416 do not damage the esophagus. One way to avoid such damage includes providing a shield on each head 420 to protect any surface that would otherwise contact the sharpened free end of head 420. As an alternative to providing a shield, each engagement member 16 may be rotatably mounted on leg 412. Thus, during insertion, engagement members 416 would lie substantially along legs 412 in a direction parallel to the longitudinal axis of ring 411. Legs 412 may include a recessed housing for receiving engagement member 416. Once ring 411 is placed with respect to the esophagus, engagement members 416 can be rotated to a position perpendicular to legs 412. Other suitable mechanisms for preventing damage to the esophagus from engagement members 416 during insertion into the esophagus are within the scope of this invention.

Referring to FIG. 10, mounting device 410 is then positioned relative to the esophagus such that ring 411 engages the inner surface of the esophagus and free ends 415 of legs 412 are disposed below the opening of the esophagus into the stomach. Mounting device 410 should be positioned with respect to the esophagus so that grooved portions 414 of legs 412 are slightly lower than the seat of the tissue fold to be secured. Preferably, a frictional fit occurs between ring 411 and the esophagus. However, sutures or other suitable securing means may also be used to secure ring 411 to the esophagus. A-Frame grasper-overtube 100 is also illustrated in FIG. 10 with grasping arm 122 folding a section of tissue. Extending through overtube 110 of A-Frame grasper-overtube 100 is a clip actuation mechanism 422 for folding legs 412 of mounting device 410. Clip actuation mechanism 422 may be formed in any conventional manner so long as it is capable of urging legs 412 to secure the tissue fold. For example, as illustrated in FIG. 10, clip actuation mechanism 422 may include a pivoting member for urging legs 412 into engagement with the folded tissue.

With a fold of tissue created between the fundus wall and the esophagus wall, using a device such as the A-frame grasper-overtube, or other suitable folding device, free end 415 is then folded up such that the surface of leg 412 on which engagement member 416 is disposed engages the exterior surface of the tissue fold. Legs 412 can be folded by clip actuation 422 mechanism extending through lumen 130 of A-frame grasper-overtube 100. The clip actuation mechanism is actuated to force leg 412 to pivot about grooved portions 414 and engage the folded tissue. Free end 415 is moved toward ring 411 with a force sufficient for head 420 to pierce the tissue fold and pass through aperture 413. Once head 420 passes through aperture 413, leg 412 secures the tissue fold in place at that location. The engaged relationship between engagement member 416 and aperture 413 also assists in holding ring 411 in place with respect to the esophagus. Each of the legs 412 provided on ring 411 will be folded in the same manner to secure a uniform fold of tissue around the perimeter of the esophagus. Once mounting device 410 has been secured to the tissue fold, the flexible delivery tube or other delivery device can be removed from the esophagus. As the delivery tube is removed, mounting device 410 will be released from the exterior of the flexible tube.

The final placement of mounting device 410 after completion of the fundoplication procedure is shown in FIG. 11. Due to the cross-sectional perspective, only two legs 412 are shown. Preferably, legs 412 each have the same length such that, when mounting device 410 is installed to secure the tissue fold, a tissue fold having a uniform depth is created around the esophagus. Furthermore, the mounting device causes alignment of the tissue clips in a radial and vertical direction around the esophageal opening into the stomach to avoid torsional stresses on the tissue after securing the fold.

An alternative manner of placing mounting device 410 to secure the tissue fold includes creating the fold of tissue during the step of folding legs 412. This procedure includes inserting the mounting device using the flexible tube as described above, followed by inserting through the tube an actuatable grasping and folding device, similar to the grasping arm of the A-frame grasper-overtube. Once the actuatable grasping and folding device has been inserted, it is positioned with respect to a leg 412 of mounting device 410 and actuated such that free end 415 of leg 412 is rotated up toward ring 411. As leg 412 rotates toward ring 411, tissue to be folded will be grabbed by the leg and brought toward the esophagus to create the tissue fold. Legs 412 will then be secured to hold the tissue fold by inserting engagement member 416 with aperture 413. To avoid damage to tissue by engagement member 416, as a result of folding leg 412, engagement member 416 could be housed within leg 412 and deployable through a spring-activated mechanism. Other suitable deploying or protection mechanisms could also be used to prevent tissue from being damaged by engagement member 416 during folding of leg 412 and are within the scope of this invention. According to one embodiment of the present invention, legs 412 may be formed with different lengths. The shorter length legs may be used to secure a fold where the curvature of the stomach near the esophagus is smaller.

Figure 12:
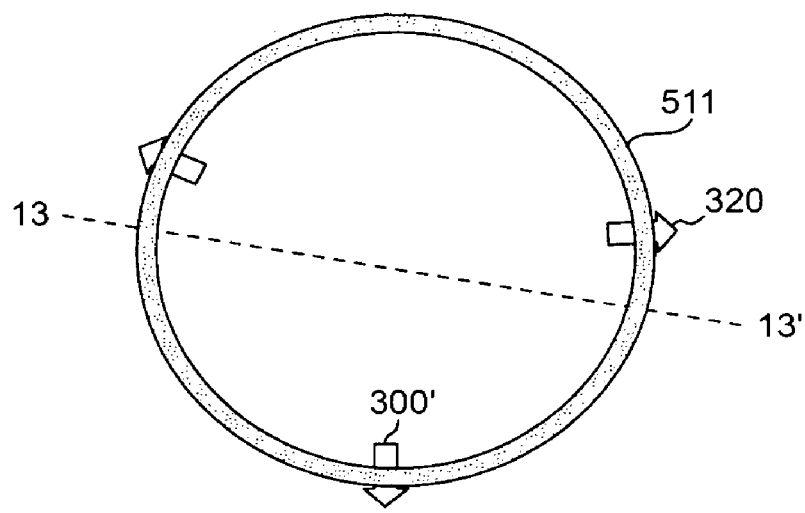
FIG. 12 is a top view of a mounting device according to another embodiment of the present invention.
Figure 13:
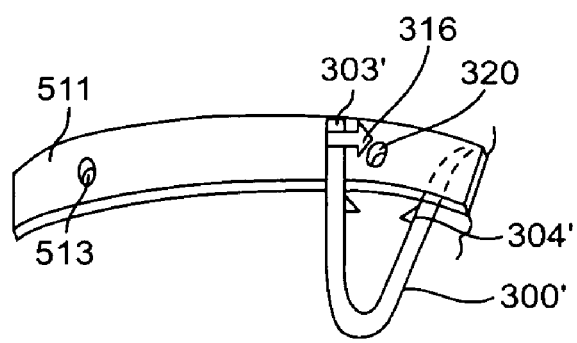
FIG. 13 is a side cross-sectional view of the mounting device of FIG. 12 taken through plane 13-13' with a tissue clip shown for engagement with the ring.
Figure 14:
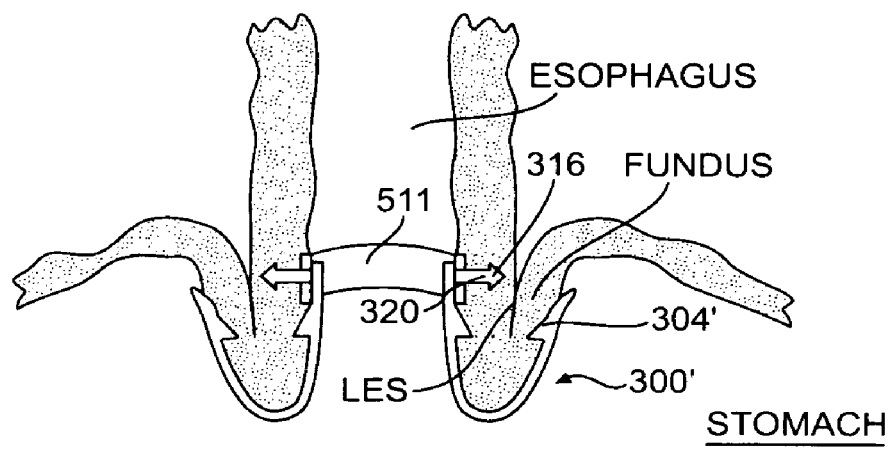
FIG. 14 is a vertical cross-sectional view of the mounting device of FIGS. 12 and 13 installed to secure a tissue fold formed by the fundus wall and esophagus wall.

Another embodiment of a mounting device according to the present invention is shown in FIGS. 12-14. The mounting device shown in these Figures essentially includes a ring 511 configured to be used with tissue clips that are substantially similar to tissue clip 300 described with reference to FIGS. 6 and 7. Tissue clip 300 shown in FIGS. 6 and 7 is a particularly suitable embodiment of a fastening mechanism for use in securing tissue during Endoscopic Fundoplication.

FIGS. 12-14 show a ring 511 configured to be used with tissue clips having substantially similar structure to tissue clips 300. In this embodiment, the tissue clip and ring 511 are not manufactured to be an integral piece. Rather, tissue clips 300' shown in FIGS. 12-14 are configured to detachably engage with ring 511 along its peripheral surface. Ring 511 includes apertures 513 spaced at various intervals around the peripheral surface of the ring. Apertures 513 extend through ring 511 in a direction perpendicular to the longitudinal axis of the ring. In the embodiment shown, three apertures 513 are disposed substantially evenly-spaced around ring 511. However, any number of apertures can be provided depending on the desired fold configuration, the thickness of the fold, and other similar factors.

Apertures 513 have a size and shape that allow them to receive an engagement member 316 disposed on arm 301' of tissue clip 300' to lock the clip into place on ring 511. Engagement member 316 engages aperture 513 in a manner similar to the way in which engagement member 416 engages aperture 413, as described with reference to the embodiment shown in 9-11. Once inserted through aperture 513, a head portion 320 of engagement member 316 is configured to pierce the tissue of the tissue fold being secured. Positioning ring 511 within the esophagus, in a manner to be described shortly, results in a vertical alignment of apertures 513 with respect to the esophagus. Thus, when engagement members 316 are locked through apertures 513 of ring 511 and into the tissue fold to be secured, tissue clips 300' also will be aligned vertically with respect to each other. Placement of tissue clips 300' utilizing ring 511 thus results in both radial and vertical alignment in the esophagus, thereby creating a uniform tissue fold.

Alternatively, apertures 513 could be replaced with engagement recesses similar to engagement recesses 413' described with reference to FIG. 9A. In such an embodiment, engagement members 316 would not extend through ring 511 to pierce the tissue of the tissue fold. Rather, the frictional fit between tissue clip 300' and the tissue to be secured, as well as the engagement between barbs 304' and the tissue, would secure the tissue fold with tissue clip 300'.

As described with reference to mounting device 410 in FIGS. 9-11, ring 511 and tissue clips 300' can be made of any suitable material that is biocompatible. Preferably, a bioabsorbable material is used so that the device will disintegrate after a certain time period sufficient for the natural adhesion of the tissue of the tissue fold to occur. Additionally, different materials may be used for ring 511 and tissue clips 300', for example, ring 511 may be formed of a flexible material such as silicone or polyurethane, while clips 300' may be formed of bioabsorbable material such as polyactic acid or polyglycolic acid. In this way, ring 511 can have sufficient flexibility to allow the esophagus to close, while clips 300' have sufficient rigidity to secure the tissue fold.

The following describes the use of ring 511 and tissue clips 300' to perform a medical procedure, such as, for example, Endoscopic Fundoplication. Initially an endoluminal device, such as, for example, a flexible tube or an A-frame grasper overtube, is inserted through the esophagus and into the stomach to provide access to the fundus. Ring 511 is then inserted within the endoluminal device using either an endoscopic gripper of the type discussed with reference to ripping tab 303' on tissue clip 300' or by placing ring 511 on the exterior of the flexible tube. Preferably, ring 511 comprises a flexible material that enables it to compress if it is necessary to insert the ring through the endoluminal device. Thus, ring 511 can be made of an elastomeric material that also is biocompatible, such as silicone or polyurethane. When placed within the esophagus, ring 511 should be configured to form a frictional fit between its peripheral surface and the inner surface of the esophagus to prevent the ring from sliding, yet should not interfere With the esophageal passage. Aside from the frictional fit, however, the engagement of engagement members 316 and the esophagus occurs through apertures 513 and assists in holding ring 511 in place. Additionally, sutures or other suitable securing means can be implemented to secure ring 511 to the esophagus if necessary.

Engaging tissue clips 300' with ring 511 may occur either before or after ring has been positioned within the esophagus. Placing tissue clips 300' after ring 511 has been installed preferably includes inserting the clips using A-frame grasper-overtube 100 as described with reference to FIG. 6A, although other endoluminal devices may be used as well. In this manner, tissue clips 300' are pulled up to seat the tissue fold between the two arms of the tissue clip in such a way so as to align engagement member 316 with an aperture 513 on ring 511. Once aligned, tissue clip 300' can be manipulated, via a gripper, to force engagement member 316 through aperture 513 and into the tissue fold. This process is repeated until all of the tissue clips have been installed and engaged with the corresponding apertures.

It is also contemplated that engagement member 316 could pass through the entire thickness of the tissue fold to engage with a fixation hole 305' on arm 302'. In this case, fixation hole 305' and engagement member 316 also would be configured to restrict passage of engagement member 316 through fixation hole 305' once engagement member 316 has been inserted into fixation hole 105'.

Tissue clips 300' also may be attached to ring 511 before ring is placed around the esophagus.

In using any of the embodiments of the mounting devices according to the present invention, a sclerosing agent may be added after installation of the devices to promote the natural adhesion of the tissue forming the tissue fold. It is preferable to select materials for the various parts of the mounting devices that disintegrate after a time period long enough for the tissue of the tissue fold to have adhered together.

It will be apparent to those skilled in the art from consideration of the specification and practice of the invention disclosed herein that various modifications and variations can be made in the mounting devices of the present invention. For example, the tissue clips, whether in the form of legs integral with the ring or in the form of separate members, may be provided in different sizes, for example, small, medium, and large, for use with children, average-sized, and larger patients, respectively. Additionally, the number of tissue clips and corresponding apertures can be changed according to the dimensions of the fold to be secured. Also, it is contemplated that the mounting devices disclosed can be installed in an open or laparascopic procedure rather than endoluminally installed.

Furthermore, the particular use of both the tissue clip and the ring in conjunction with the A-frame grasper-overtube device and Endoscopic Fundoplication procedure are illustrative only. It is considered to be within the scope of this invention to use these devices with other endoluminal procedures, as well as for purposes outside of the medical industry that may require insertion, alignment, and installation of fasteners or material manipulators through small spaces.

Addressing another aspect of the present invention, a technique for folding and thereby thickening esophageal tissue and reducing the diameter of the esophageal opening in the region of the LES to treat GERD is accomplished through another endoluminal medical procedure. The endoluminal device used in this procedure is configured for insertion through the esophagus to create a generally longitudinal tissue fold and then securing the fold. As with the procedures described above, this endoluminal procedure has the benefits of being less invasive, quicker, and less expensive as compared to previous techniques.

As with most endoluminal procedures, completion of the folding and securing procedure preferably occurs as rapidly as possible without compromising the safety or non-invasiveness of the procedure. To maintain the procedure as relatively non-invasive, it is preferable to provide a device that is relatively small in size, yet has the capability to secure tissue in the esophagus in a plurality of locations and with consistent results. In addition, a catheter need only be inserted once and the device can easily be removed, reloaded and reinserted to secure tissue around the circumference of the esophagus.

To accomplish these objectives, a suction stapler configured for endoluminal insertion is used to create and secure tissue folds. The suction stapler, and method for its use, are particularly suited for performing a medical procedure in which tissue is folded and secured in the region of the LES. Using the inventive device to secure the esophageal tissue allows the procedure to be performed rapidly and relatively non-invasively, and results in a substantially uniform tissue fold.

Although the inventive device and method will be discussed mainly with reference to securing esophageal tissue in the region of the LES, the device and method can be employed in conjunction with other medical procedures that require creating and securing tissue folds. Moreover, the device and method are applicable in other settings, including industrial settings, that require the securing of two surfaces together in an environment having limited access to the two surfaces.

An embodiment of a suction stapler 610 according to the present invention is shown in FIGS. 15A-15c. Suction stapler 610 includes an outer tube 611 defining a lumen 612. Toward its distal end, outer tube 611 includes a sidewall opening 613 extending along a portion of outer tube 611. Opening 613 has an axial length at least as long as the length of a tissue clip to be described, such as, for example, approximately 2 to 4 cm. Opening 613 has a width sufficient to provide a suction force to draw a portion of esophageal tissue therein, as will also be described, such as, for example, approximately 7 mm. Outer tube 611 is hollow and sealed at a distal end 616.

Within lumen 612 is a rotatable inner sleeve 615. Inner sleeve 615 is hollow and has a semi-circular configuration at least along an axial length of its distal end corresponding to opening 613. Otherwise, sleeve 615 can have a completely circular or substantially circular cross-section. As shown most clearly in FIGS. 15A and 15B, the semi-circular configuration allows inner sleeve 615 to close and open opening 613 as the sleeve rotates within outer tube 611.

At a proximal end (not shown) of the suction stapler, a vacuum source connects to a fitting disposed on outer tube 611. When initiated, the vacuum source creates a suction force at sidewall opening 613 in tube 611. Also disposed at the proximal end of outer tube 611 is an actuator for rotating outer tube 611 and inner sleeve 615 relative to one another. Such an actuator can either be manually or automatically controlled. Such vacuum fittings and proximal actuators may be of any type known in the art, such as, for example the vacuum fitting 625 and rotation actuator 626 illustrated in FIG. 15A.

Outer tube 611 and inner sleeve 615 preferably are made of metal or other suitable like material capable of withstanding the suction force generated by the vacuum source, permitting relative rotational motion, and sufficiently flexible to the extent through the esophagus and, for example, through an endoscope. For example, outer tub 611 and inner sleeve 615 may be formed of metal braid and coil reinforced polymers such as nylon, polyamide, or nylon block copolymers. The diameter of lumen 612 of outer tube 611 may be approximately 10 mm.

FIG. 16 shows an embodiment of a tissue clip 616 that can be deployed using suction stapler 610. In the embodiment shown, tissue clip 616 includes a female part 617 and a male part 618. Female part 617 extends lengthwise and defines a number of holes 619 that correspond in number and position to darts 620 disposed on male part 618. Darts 620 and holes 619 are configured so that darts 620 can be inserted in a first direction through holes 619 when female part 617 and male part 618 are disengaged. Once darts 620 have been inserted through holes 619, female part 617 and male part 618 are in an engaged relationship and darts 620 cannot be pulled back through holes 620 in a second direction opposite to the first direction.

FIG. 16 shows female part 617 and male part 618 including five holes and darts, respectively. However, any number, rows, columns, or distribution of corresponding holes and darts may be used depending on such factors as the amount of tissue to be secured, the positioning of the clip, and other similar factors. Tissue clip 616, including both female part 617 and male part 618, preferably is made of a biocompatible material, and in particular of a bioabsorbable material. Utilizing a bioabsorbable material enables tissue clip 616 to disintegrate safely within the body after the tissue surfaces being secured together by clip 616 have had an opportunity to form a natural adhesion.

Figure 17:
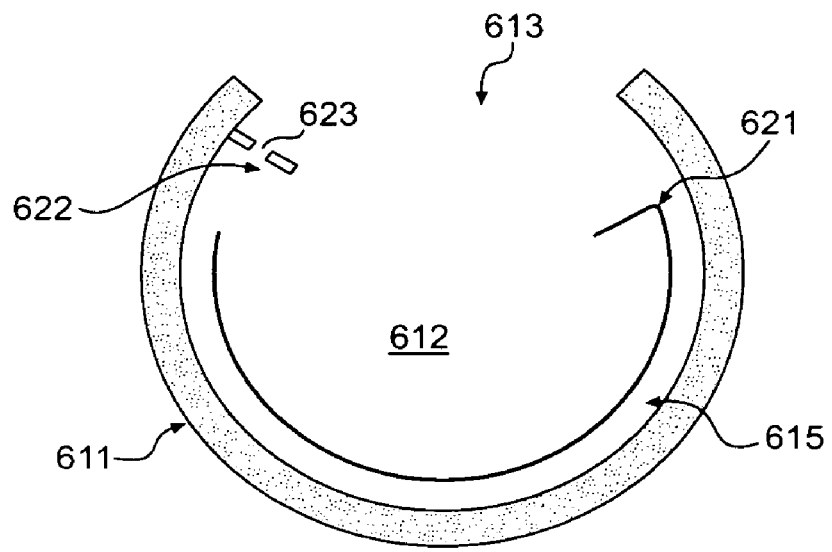
FIG. 17 is a cross-sectional view taken through plane 17-17 in FIG. 15a showing details of the internal structure of the suction stapler according to an embodiment of the present invention.
Figure 18:
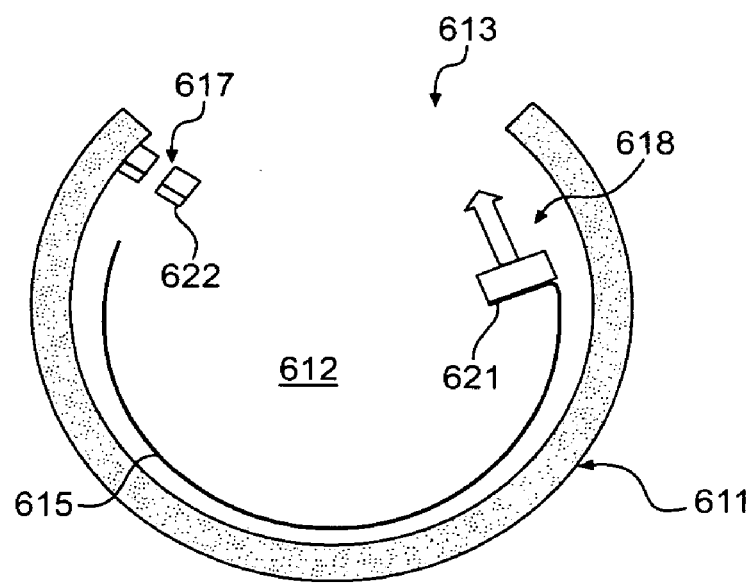
FIG. 18 is a view of the suction stapler of FIG. 17 with the male and female parts of the tissue clip inserted according to an embodiment the present invention.

FIGS. 17 and 18 best show the general placement of female part 617 and male part 618 in suction stapler 610 prior to their deployment to secure tissue. The Figures show a cross-sectional view of outer tube 611 and inner sleeve 615 in the region of sidewall opening 613 and taken through plane 17-17 shown in FIGS. 15A-15c. As shown in these Figures, inner sleeve 615 includes a first small lip or ledge 621 formed at the edge defining the semi-circular opening and configured to hold and push male part 618. Ledge 621 may include a protrusion or recess for securely engaging a similarly sized recess or protrusion in male part 618. Lip 621 is positioned proximate one edge of sidewall opening 613 of outer tube 611 when inner sleeve 615 is rotated to completely open opening 613. For holding female part 617 prior to installation of tissue clip 616, outer tube 611 includes a second small lip or ledge 622 positioned on its inner surface near an edge of opening 613. Thus, lip 622 is positioned opposite to the edge of opening 613 by which lip 621 is positioned when inner sleeve 615 is rotated to the completely open position. Lip 622 defines an aperture 623 located substantially at a center thereof. Aperture 623 aligns with holes 619 when lip 622 holds female part 617, as shown in FIG. 18. Thus, aperture 623 accommodates the tip of dart 620 during the insertion of dart 620 through hole 619 to engage female part 617 and male part 618. Although the Figures show female part 617 being held by ledge 622 disposed on outer tube 611 and male part 618 by lip 621 disposed on inner sleeve 615, female part 617 could be held instead by inner sleeve 615 and male part 618 by outer tube 611. Regardless of which element holds female part 617, an aperture should be provided that aligns with holes 619. Lips 621 and 622 also limit the relative rotational displacement of tube 611 and sleeve 615.

Figure 19:
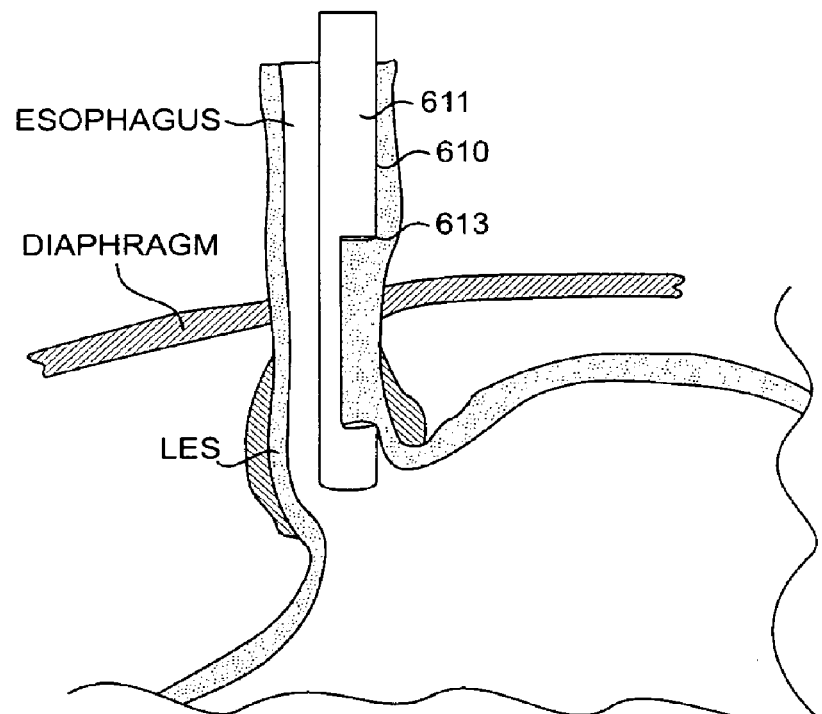
FIG. 19 is a vertical, cross-sectional view of the suction stapler according to an embodiment of the present invention inserted into the esophagus to suck the esophageal tissue into the side wall opening of the device.
Figure 20:
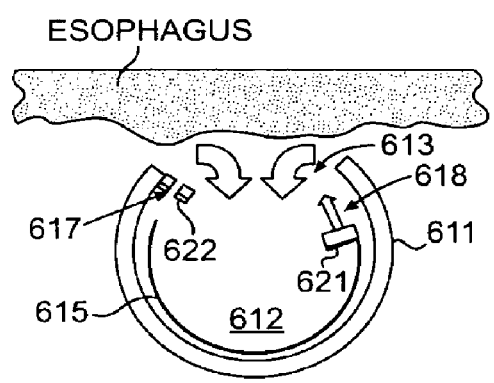
FIG. 20 is a cross-sectional view of the suction stapler and inserted tissue clip according to an embodiment of the present invention, with placement of the stapler relative to a portion of esophageal tissue to be secured and suction being drawn through the stapler.
Figure 21:
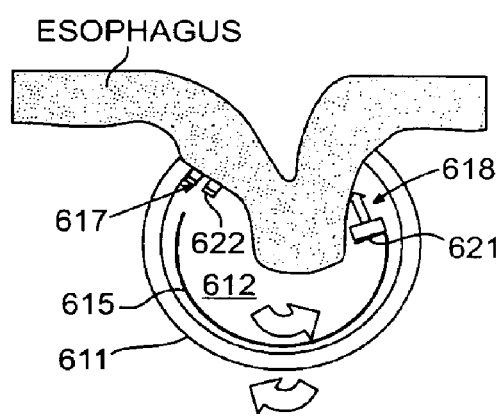
FIG. 21 is a cross-sectional view of the suction stapler and esophageal tissue shown in FIG. 20 with the tissue being sucked into the opening in the suction stapler and arrows showing the relative rotation of the inner sleeve and the outer tube to deploy the male and female parts of the tissue clip according to an embodiment of the present invention.
Figure 22:
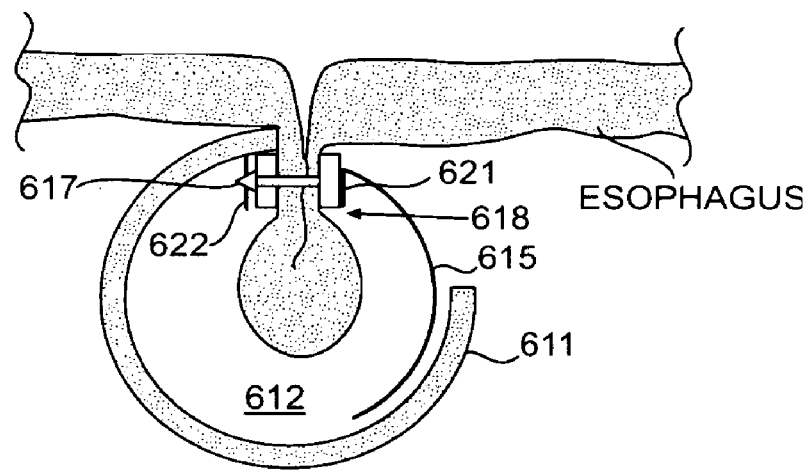
FIG. 22 is a cross-sectional view of the suction stapler and secured esophageal tissue after the inner sleeve and outer tube have been fully rotated to engage the male and female parts of the tissue clip to secure the tissue fold according to an embodiment of the present invention.

Installation of tissue clip 616 to secure a fold of esophageal tissue during the medical procedure according to the present invention will now be described with particular reference to FIGS. 19-21 FIG. 19 shows suction stapler 610 inserted through a patient's esophagus, with its distal end positioned proximal to the opening of the esophagus into the stomach. As shown, sidewall opening 613 is positioned close to the esophagus wall that includes the tissue to be folded and secured. Suction stapler 610 can be inserted either directly into the esophagus or through an endoscope. If the stapler is inserted directly through the esophagus, a viewing mechanism in the form of an optical fiber or the like may be inserted through lumen 612 for initial positioning of the stapler with respect to the esophagus wall. Once stapler 610 is positioned, the viewing mechanism can be removed.

Upon proper positioning of sidewall opening 613 with respect to the esophagus, as shown in FIGS. 19 and 20, the vacuum source is turned on to create suction through opening 613 and outer tube lumen 612. The arrows in FIG. 20 illustrate the direction of the suction force with respect to opening 613 and inner sleeve 615. Upon proper positioning of stapler 610, the suction force acts on the esophagus wall to suck esophageal tissue through opening 613 and into the hollow space defined by inner sleeve 615, as shown in FIG. 20. The strength of the suction force should be sufficient to suck the esophageal tissue into stapler 610, but should be gentle enough to avoid tearing or otherwise damaging the tissue.

Once the desired tissue fold has been created within inner sleeve 615, as shown in FIG. 21, installation of tissue clip 616 to secure the fold proceeds in the following manner. First, actuation of inner sleeve 615 and outer tube 611 occurs through the actuation member disposed at the proximal end of suction stapler 610. The actuation member causes inner sleeve 615 to rotate in one direction and outer tube 611 to rotate in another, as shown by the arrows in FIG. 21. That is, inner sleeve 615 rotates in a direction such that female part 617 moves toward male part 618. Accordingly, outer tube 611 rotates in a direction opposite to inner sleeve 615 such that male part 618 moves toward female part 617. It only may be necessary to rotate one of the tube 611 and sleeve 615, rather than both.

Figure 23:
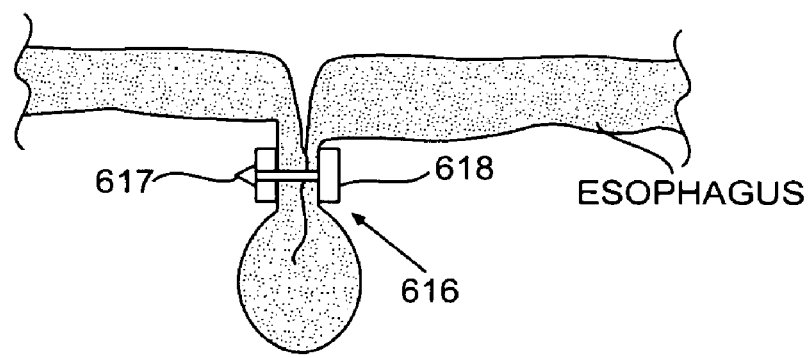
FIG. 23 is a cross-sectional view of a portion of the esophageal wall with a tissue clip installed to secure the tissue fold after having been deployed using the suction stapler according to an embodiment of the present invention.
Figure 24:
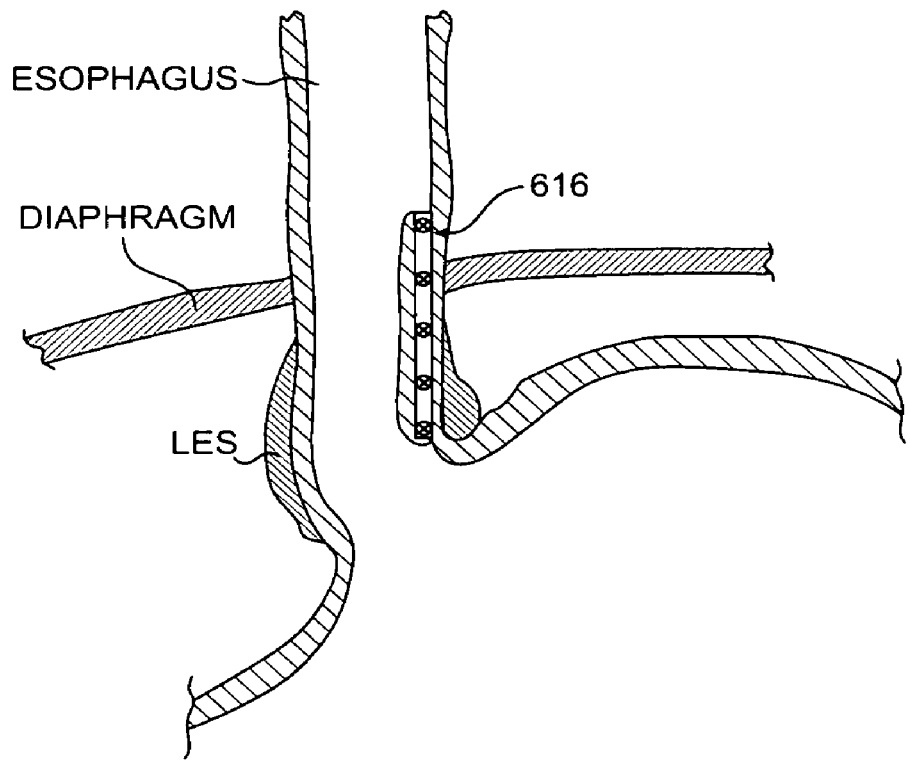
FIG. 24 is a vertical, cross-sectional view of a portion of the esophagus and stomach showing the installation of the tissue clip to secure the fold of esophageal tissue according to an embodiment of the present invention.
Figure 25:
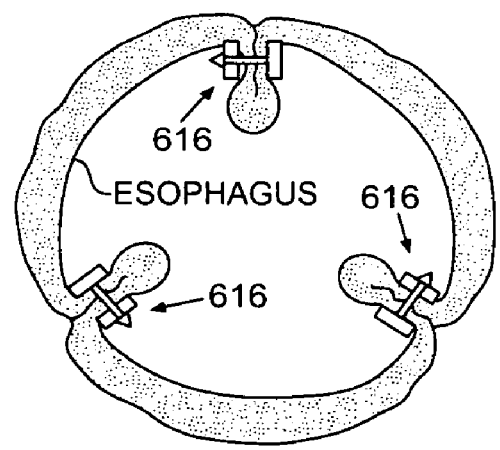
FIG. 25 is a cross-sectional view of the entire circumference of the esophagus showing tissue clips installed at three spaced radial intervals around the esophagus according to an embodiment of the present invention.

The relative rotation of inner sleeve 615 and outer tube 611 continues until darts 620 on male part 618 pierces and extends through the tissue fold and is driven through apertures 619 in female part 617. After such engagement of female part 617 and male part 618, inner sleeve 615 and outer tube 611 are again counter-rotated to return to their original positions. Upon the return of inner sleeve 615 and outer tube 611 to their original positions, the vacuum source is turned off and suction stapler 610 is removed from the esophagus. The force resulting from the engagement of female part 617 and male part 618 overcomes the force holding female part 617 and male part 618 to outer tube 611 and inner sleeve 615, respectively. Thus, as shown in FIG. 23, tissue clip 616 remains to secure the tissue fold after removal of suction stapler 610. FIG. 25 shows a vertical cross-sectional view of the esophagus with three tissue clips 616 in place to secure tissue folds. If tissue clip 616 is made of bioabsorbable material, it eventually disintegrates after a time period sufficient to allow natural adhesion of the surfaces of the tissue fold.

If more tissue folds need securing, the suction is turned off, suction stapler 610 is removed, reloaded with staples, and reinserted into the esophagus. Suction stapler 610 can be reinserted to a new position relative to the circumference of the esophagus. When sidewall 613 has been placed in the new position, the vacuum source is initiated and the stapling procedure repeated as described above.

The suction stapler also may be modified to incorporate a magazine-type loading of staples or other assembly of multiple staple loads so that the suction stapler does not need to be removed to initiate and secure more than one tissue fold around the circumference of the esophagus. In this way, the suction stapler can permit the installation of a plurality of tissue clips 616 around the circumference of the esophagus during a single insertion of the device and perform the thickening and tightening technique in a relatively quick and non-invasive manner. For instance, FIG. 25 shows the installation of three tissue clips to secure tissue folds at evenly-spaced intervals around the esophagus. Of course, any number of tissue folds at any desired spacing may be created as required to achieve the desired increase in tissue thickening of the esophageal region and reduction in diameter of the opening of the esophagus.

Further, metal staples could be used in place of tissue clips 616. In this embodiment, lip 621 would be replaced by a staple pusher, and lip 622 would be replaced with a staple forming anvil. Thus, rotation of outer tube 611 with respect to inner sleeve 615 would cause a metal staple to be urged against the anvil to deform the staple and secure the tissue fold. This embodiment would not require the use of female part 617 as described above.

It will be apparent to those skilled in the art from consideration of the specification and practice of the invention disclosed herein that various modifications and variations can be made in the stapling device of the present invention. For example, the tissue clip used in conjunction with the stapling device may be provided in different sizes, such as, for example, small, medium, and large, for use with children, average-sized, and larger patients, respectively. However, it is important that the entire device be configured to fit in the esophagus, or other part of the body, depending on the particular endoluminal procedure being performed. Additionally, as already mentioned the number of tissue clips installed to secure tissue folds may be altered. Moreover, other lumens may be provided in the tube so that additional devices may be inserted into the esophagus and stomach to perform additional operations.

The particular use of both the tissue clip and the stapling device in conjunction with a LES folding and securing procedure is illustrative only. It is considered to be within the scope of this invention to use these devices with other endoluminal procedures, as well as for purposes outside of the medical industry that may require insertion and installation of fasteners through small spaces.

Figure 26:
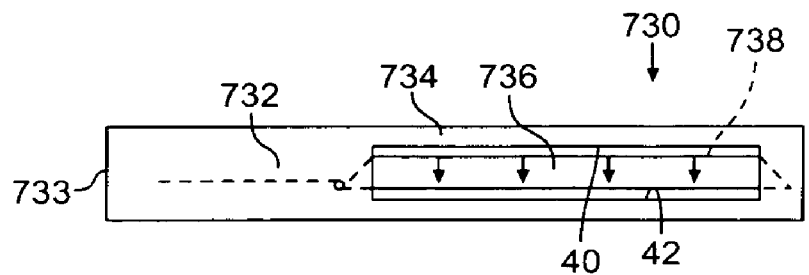
FIG. 26 is a perspective view of a suction-grasper device according to the present invention.

In accordance with yet another aspect of the present invention, a suction-grasper device, general indicated at 730 in FIG. 26, is an endoscopic tool used to manipulate tissue. Suction-grasper device 730 performs a portion of an endoluminal GERD procedure, but has applications in many endoscopic, laparoscopic or percutaneous procedures. Suction-grasper device 730 acts to grasp esophageal tissue and draw it into the lumen 733 of cannula 732. In particular, suction grasper 730 is beneficial in assisting in GERD procedures which are complicated by a herniated esophageal tissue, where the tissue has bulged and protruded above the diaphragm (a hiatal hania). In the instance of a hiatal hernia, the tissue must be grasped and pulled downward toward the stomach. Suction-grasper device 730 accomplishes this task by initially grabbing the esophageal tissue by way of suction and then securing the tissue to allow manipulation of the tissue that suction alone could not achieve.

Figure 27:
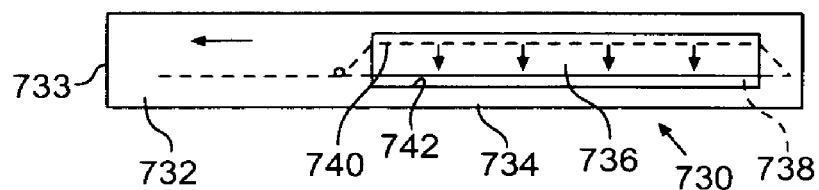
FIG. 27 illustrates the operation of the suction-grasper device after tissue has been located therein.

As illustrated in FIGS. 26 and 27, suction-grasper device 730 includes a flexible, possibly reinforced, polymer cannula 732 having a central lumen 733, a sealed distal end 734 and a longitudinal window 736 cut or formed into distal end 734 of cannula 732. Distal end 734 may include a housing or cap fixedly attached to cannula 732. Window 736 may be about 4 cm long and cover about ⅓ of the external circumference of suction-grasper device 730. Suction applied to a proximal end (not shown) of cannula 732 results in a vacuum created at the area of window 736.

According to one embodiment of the present invention, grasping the tissue suctioned through window 736 into cannula 732 takes place with a grasping mire 738 which extends across the length of window 736 and back to the proximal end of the cannula 732. Wire 738 is aligned such that in the free, non-tensioned position, wire 738 does not impinge upon a open area of the window 736. However, once tensioned by an operator at the proximal end of the instrument, wire 738 moves into an intermediate position between the longitudinal edges 740, 742 of the window 736, thereby securing or grasping the tissue.

Grasping wire 738 may be formed in cannula 732, or integrated into the above mentioned housing or cap. Further, grasping wire 738 can carry a serrated tube to assist in fixing the tissue in window 736.

Suction-grasper device 730 acts in the following manner with respect endoluminal treatment of GERD. Suction-grasper device 730 is inserted into the esophagus with suction window 736 located towards the esophageal tissue. When suction is applied to the suction-grasper device 730, tissue is drawn toward window 736 of suction-grasper 730. When the tissue is sufficiently positioned within lumen 733 and window 736 of suction-grasper device 730, tension is applied to the proximal end of grasping wire 738. Due to, for example, an eccentric alignment of wire contact points within cannula 732, tensioned wire 738 will be moved to within window 736 and in contact with the tissue. As further force is applied to wire 738, the tissue is securely grasped.

Figure 28:
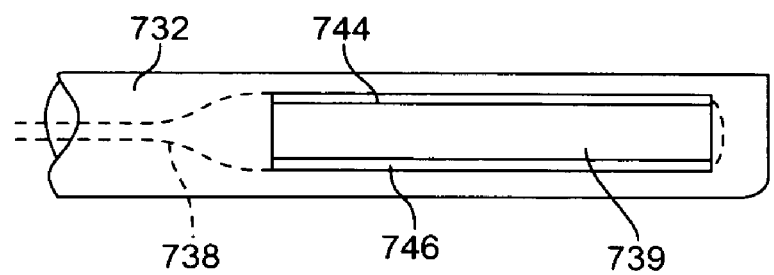
FIG. 28 is a perspective view of an alternative embodiment of a suction-grasper device according to the present invention.

It is appreciated that there are various alternative arrangements for securing the wire 738 so that tension from the operator causes the wire to fix the tissue within window 736. For Example, as shown in FIG. 28, grasping wire 738 may be wrapped around a grasping plate 739 so that the pulling of grasping wire 738 causes the grasping plate to secure the tissue. In this embodiment, grasping plate 739 may be formed in a generally U-shaped or C-shaped configuration and tension of the grasping wire 738 would cause the open ends 744 and 746 of the grasping plate 739 to close and secure the tissue. Alternatively, grasping wire 738 could be coupled to cannula 732 above and below grasping plate 739 and wrapped around only one open end of grasping plate 739. In this configuration, tension of grasping wire 738 would urge one open end of grasping plate 739 toward the opposing open end and thus secure the tissue.

Once the tissue is grasped, suction-grasper device 730 is advanced proximally along the esophagus, to take up and straighten out the loose tissue created by the hiatal hernia, and position the tissue where desired. Advancing the tissue may take a bit of force, thereby necessitating the use of grasping wire 738. Suction-grasper device 730 may then release the tissue by releasing the grasping wire and then cutting off the vacuum supply.

Grasping wire 738 has been found to be an extremely effective mode of grabbing and positioning a length of tissue in the procedure described above. The device allows a large amount of longitudinal force to be applied to the esophageal tissue without losing the secure grip of suction-grasper device 730.

There are other possible embodiments of components to grasp the tissue within suction-grasper device 730, including (but not limited to) a coaxial tube with a window, aligned with window 736, such that upon tissue being located within both windows (by suction or otherwise), rotation of the coaxial tube relative to window 736 would cause the edges of the coaxial tube to grasp the tissue located between the coaxial tube and suction-grasper cannula 732. Instead of a coaxial tube, a sliding flap may be included in cannula 732 to fix tissue in window 736.

Distal end 734 of suction-grasper device 730 may include a clear section of cannula 732 formed opposite window 736. Clear section would allow for visual confirmation of tissue being sucked through window 736 into cannula 732. Such visual confirmation could be achieved by way of, for example, an endoscope. Alternatively, the whole device may be fabricated of a clear material.

Suction-grasper device 730 is not restricted in use to the treatment of GEM. Suction-grasper tool 730 is not absolutely necessary to treat GERD, but is especially suited for assisting a treatment of GERD that is complicated by a hiatal hernia. As noted above, suction-grasper device 730 may be utilized in any endoscopic, laparoscopic, endoluminal or percutaneous procedure requiring tissue manipulation.

The invention described above, in its broader aspects, is not limited to the specific details and illustrative examples shown and described in the specification. It is intended that departures may be made from such details without departing from the true spirit or scope of the general inventive concept as defined by the following claims and their equivalents.

What is claimed:

1. A method of creating a tissue fold comprising:
   inserting an endoscope and a grasper-overtube through an esophagus and at least partially into a stomach cavity, the grasper-overtube including a tube, disposed radially outward and around the endoscope, and an arm movably mounted relative to the tube;
   positioning the arm of the grasper-overtube at a first position radially outward from the tube, forming a first angle between the arm of the grasper-overtube and the tube;
   establishing native tissue between the arm of the grasper-overtube and a portion of the tube; and
   positioning the arm of the grasper-overtube at a second position radially outward from the tube, forming a second angle between the arm of the grasper-overtube and the tube, the second angle being smaller than the first angle;
   grasping the native tissue and forming the tissue fold;
   inserting a tissue fastener through a lumen of the tube and an opening at a distal end of the tube, the tissue fastener having a first arm and a second arm coupled to the first arm of the tissue fastener; and
   securing the tissue fold with the tissue fastener, the first arm of the tissue fastener engaging a first outer surface of the tissue fold and having a free end positioned on a first side of the tissue fold, and the second arm of the tissue fastener engaging a second outer surface of the tissue fold and having a free end positioned on a second side of the tissue fold opposite the first side of the tissue fold.

2. The method of claim 1, wherein the tissue fastener is a clip.

3. The method of claim 1, further including moving the grasper-overtube in a direction toward the opening of the esophagus in the stomach to establish the native tissue between the arm of the grasper-overtube and the tube.

4. The method of claim 1, further including positioning the arm of the grasper-overtube at the second position to clamp the tissue fold.

5. The method of claim 1, wherein the native tissue is part of any one of a fundus of the stomach or a lower esophageal sphincter.

6. The method of claim 1, further including rotating the grasper-overtube about a longitudinal axis of the endoscope.

7. The method of claim 1, further including visualizing the native tissue while positioning the arm of the grasper-overtube relative to the tube.

8. The method of claim 1, further including pivoting the arm of the grasper-overtube relative to the tube in a direction away from a longitudinal axis of the endoscope to form the first angle and pivoting the arm of the grasper-overtube in a direction toward the longitudinal axis of the endoscope to form the second angle.

9. The method of claim 1, wherein a distal portion of the tube is clear.

10. The method of claim 1, wherein the tissue fastener is a one-piece fastener.

11. A method of forming and securing a tissue fold with a tissue manipulating device having a tubular portion disposed radially outward relative to an endoscope and an arm movably mounted relative to the tubular portion, the method comprising:
   inserting the endoscope and the tissue manipulating device through an esophagus and at least partially into a stomach cavity;
   pivoting the arm of the tissue manipulating device from a first position generally aligned with the tubular portion to a second position to form an angle between the arm of the tissue manipulating device and the tubular portion;
   positioning native tissue between the arm of the tissue manipulating device and the tubular portion;
   pivoting the arm of the tissue manipulating device to decrease the angle between the arm of the tissue manipulating device and the tubular portion to grasp the native tissue and form the tissue fold; and
   securing the tissue fold with a one-piece fastener having a first arm and a second arm coupled to the first arm of the tissue fastener, the first arm of the tissue fastener engaging a first outer surface of the tissue fold and having a free end positioned on a first side of the tissue fold, and the second arm of the tissue fastener engaging a second outer surface of the tissue fold and having a free end positioned on a second side of the tissue fold opposite the first side of the tissue fold.

12. The method of claim 11, further including securing the tissue fold with two one-piece fasteners.

13. The method of claim 11, further including moving the tissue manipulating device in a direction toward the opening of the esophagus in the stomach to position the native tissue between the arm of the tissue manipulating device and the tubular portion.

14. The method of claim 11, wherein the native tissue is part of a lower esophageal sphincter.

15. The method of claim 11, further including pivoting the arm of the tissue manipulating device in a direction away from a longitudinal axis of the endoscope when pivoting the arm of the tissue manipulating device from the first position to the second position.

16. The method of claim 11, further including pivoting the arm of the tissue manipulating device in a direction toward a longitudinal axis of the endoscope when pivoting the arm of the tissue manipulating device to decrease the angle between the arm of the tissue manipulating device and the tubular portion and grasp the native tissue.

17. The method of claim 11, further comprising inserting the one-piece fastener through a lumen of the tubular portion and an opening at a distal end of the tubular portion.

18. The method of claim 11, wherein a distal portion of the tubular portion is clear.

* * * * *